(12) United States Patent
Pan et al.

(10) Patent No.: US 8,987,233 B2
(45) Date of Patent: Mar. 24, 2015

(54) BRUTON'S TYROSINE KINASE ACTIVITY PROBE AND METHOD OF USING

(75) Inventors: Zhengying Pan, Alpharetta, GA (US); Shyr Jiann Li, South San Francisco, CA (US); Heleen Scheerens, Menlo Park, CA (US); Lee Honigberg, San Francisco, CA (US); Erik Verner, Belmont, CA (US)

(73) Assignee: Pharmacyclics, Inc., Sunnyvale, CA (US)

(*) Notice: Subject to any disclaimer, the term of this patent is extended or adjusted under 35 U.S.C. 154(b) by 1280 days.

(21) Appl. No.: 11/935,277

(22) Filed: Nov. 5, 2007

(65) Prior Publication Data

US 2008/0214501 A1 Sep. 4, 2008

Related U.S. Application Data

(60) Provisional application No. 60/864,350, filed on Nov. 3, 2006.

(51) Int. Cl.
| | | |
|---|---|---|
| C09B 69/00 | (2006.01) | |
| C07D 487/04 | (2006.01) | |
| G01N 33/573 | (2006.01) | |
| A61K 31/519 | (2006.01) | |

(52) U.S. Cl.
CPC ............ *C07D 487/04* (2013.01); *G01N 33/573* (2013.01); *G01N 2333/9121* (2013.01); *G01N 2500/00* (2013.01)
USPC .......................... 514/64; 514/262.1; 544/262

(58) Field of Classification Search
CPC ........................... A61K 31/519; C07D 487/04
USPC ........................................ 544/262; 514/262.1
See application file for complete search history.

(56) References Cited

U.S. PATENT DOCUMENTS

| 5,298,403 | A | 3/1994 | Danielson et al. |
| 6,660,744 | B1 | 12/2003 | Hirst et al. |
| 6,921,763 | B2 | 7/2005 | Hirst et al. |
| 2002/0016460 | A1 | 2/2002 | Snow et al. |
| 2005/0008640 | A1 | 1/2005 | Waegell et al. |
| 2007/0281907 | A1 | 12/2007 | Watkins |
| 2008/0108636 | A1 | 5/2008 | Honigberg et al. |
| 2013/0225812 | A1 | 8/2013 | Pan et al. |

FOREIGN PATENT DOCUMENTS

| WO | WO-2001-019829 A2 | 3/2001 |
| WO | WO-2001-019829 A3 | 3/2001 |
| WO | WO-01-25238 A2 | 4/2001 |
| WO | WO-2001-044258 A1 | 6/2001 |
| WO | WO-2002-080926 A1 | 10/2002 |
| WO | WO-03-081210 A2 | 10/2003 |
| WO | WO-2004-100868 A2 | 11/2004 |
| WO | WO-2004-100868 A3 | 11/2004 |
| WO | WO-2005-074603 | 8/2005 |
| WO | WO-2006-052913 A1 | 5/2006 |
| WO | WO-2006-053121 A2 | 5/2006 |
| WO | WO-2007-041712 A1 | 4/2007 |
| WO | WO-2008-039218 A2 | 4/2008 |

OTHER PUBLICATIONS

Dorwald, F. Z., Side Reactions in Organic Synthesis, 2005, preface.*
Yee et al. (The Journal of Biological Chemistry, 2005, 32(15), pp. 29053-29059).*
Arnold et al., "Pyrrolo[2,3-d]pyrimidines Containing an Extended 5-Substituent as Potent and Selective Inhibitors of Ick 1," Biorg. Med. Chem. Ltrs. 10:2167-2170 (2000).
Berkers, C.R. et al., "Activity probe for in vivo profiling of the specificity of proteasome inhibitor bortezomib," Nat. Methods 2(5):357-362 (2005).
Burchat, A.F. et al., "Pyrazolo[3,4-d]pyrimidines Containing an Extended 3-Substituent as Potent Inhibitors of Lck-a Selectivity Insight," Biorg. Med. Chem. Ltrs 12:1687-1690 (2002).
Cravatt, B.F. and Sorensen, E.J., "Chemical strategies for the global analysis of protein function," Curr. Op. Chem. Biol. 4:663-668 (2000).
Kato, D. et al., "Activity-based probes that target diverse cysteine protease families," Nature Chem. Biol. 1:33-38 (2005).
Liu, Y. et al., "Wortmannin, a Widely Used Phosphoinositide 3-Kinase Inhibitor, also Potently Inhibits Mammalian Polo-like Kinase," Chem. & Biol. 12:99-107 (2005).
Mao, C. et al., "Crystal Structure of Bruton's Tyrosine Kinase Domain Suggests a Novel Pathway for Activation and Provides Insights into the Molecular Basis of X-Linked Agammaglobulinemia," J. Biol. Chem. 276:41435-41443 (2001).
Nisitani, S. et al., "In situ detection of activated Bruton's tyrosine kinase in the Ig signaling complex by phosphopeptide-specific monoclonal antibodies," PNAS 96:2221-2226 (1999).
Qiu, Y. and Kung, H., "Signaling network of the Btk family kinases," Oncogene 19:5651-5661 (2000).
Saghatelian, A. and Cravatt, B.F., "Assignment of protein function in the postgenomic era," Nature Chem. Biol. 1:130-142 (2005).
Yee, M. et al., "A Cell-permeable, Activity-based Probe for Protein and Lipid Kinases," J. Biol. Chem. 280(32):29053-29059 (2005).
Nam et al., "ATP-phosphopeptide conjugates as inhibitors of Src tyrosine kinases," Bioorg. Med. Chem. 12(22):5753-5766 (2004).
EP 07867362 Supplemental Search Report dated Feb. 8, 2010.
Chen et al., "4,4-Difluoro-4-bora-3a,4a-diaza-s-indacene (BODIPY) dyes modified for extended conjugation and restricted bond rotations," J. Org. Chem. 65(10):2900-2906 (2000).
Mahajan et al., "Rational design and synthesis of a novel anti-leukemic agent targeting Bruton's tyrosine kinade (BTK), LFM-A13 [alpha-cyano-beta-hydroxy-beta-methyl-N-(2,5-dibromophenyl)propenamide]," J.. Biol. Chem. 274(14):9587-9599 (1999).

(Continued)

*Primary Examiner* — Susanna Moore
(74) *Attorney, Agent, or Firm* — Wilson Sonsini Goodrich & Rosati

(57) ABSTRACT

Described herein are probes for Bruton's tyrosine kinase (Btk). Such probes are used to characterize and develop Btk-selective inhibitors intended for therapeutic use.

16 Claims, 11 Drawing Sheets

(56) References Cited

OTHER PUBLICATIONS

PCT/US07/23306 Search Report dated Jul. 21, 2008.
EP 06850386.1 Search Report and Written Opinion dated Sep. 10, 2010.
Uckun and Qazi, "Bruton's tyrosine kinase as a molecular target in treatment of leukemias and lymphomas as well as inflammatory disorders and autoimmunity," Expert Opinion Ther. Patents 20(11):1-14 (2010).
Chang et al., "The Bruton tyrosine kinase inhibitor PCI-32765 ameliorates autoimmune arthritis by inhibition of multiple effector cells," Arthritis Research & Therapy 13:R115 (2011).
PCT/US10/52377 Search Report and Written Opinion mailed Jun. 29, 2011.
Apsel et al., Targeted Polypharmacology: Discovery of Dual Inhibitors of Tyrosine and Phosphoinositide Kinases, Nature Chem Bio, vol. 4(11), 2008, pp. 691-699.
Denny, "Irreversible Inhibitors of the erbB family of protein tyrosine kinases," Pharmacology Therapeutics, vol. 93, Issue 2-3, pp. 253-261 (2002).
"Handbook of Fluorescent Probes and Research Chemicals," Haugland Richard. P, Handbook of Fluorescent Probes and Research Chemicals, Molecular Probes, Eugene, OR, [U.A.], Sixth edition, pp. 13-18 (1996).
Traxler et al., Use of Pharacophore Model for the Design of EGF-R Tyrosine Kinase Inhibitors: 4-(Phenylamino)pyrazolo[3,4-d]pyrminidines, J. Med. Chem., vol. 40 (22), 1997, pp. 3601-3616.
CA 2668286 Examination Report dated Apr. 20, 2012.

* cited by examiner

Compound 1        Compound 2

Core        Linker        Bodipy FL

Compound 3

Core        Linker        Bodipy 530

Compound 4

| | | |
|---|---|---|
| Btk | RPIFIITEYMANGCLLNYLREMRHR | Q06187 |
| Bmx | YPLYLVTEYLSNGCLLNYIRSHGKG | NM_203281.1 |
| Tec | KPIYIVTEFMERGCLLNFLRQRQGH | NM_003215.1 |
| Txk | KPLYIVTEFMENGCLLNYLRENRGK | NM_003328.1 |
| Itk | APICLVTEFMEHGCLSDYLRTGRGL | D13720.1 |
| EGFR | STVQLITQLMPFGCLLDYVREHKDN | NM_005228.3 |
| Erb2 | STVQLVTQLMPYGCLLDHVRENRGR | NM_004448.2 |
| Erb4 | PTIQLVTQLMPHGCLLEYVHEHKDN | NM_005235.1 |
| Jak3 | PELRLVMEYLPSGCLRDFLQRHRAR | U70065.1 |
| Blk | EPIYIVTEYMARGCLLDFLKTDEGS | P51451 |

BRUTON'S TYROSINE KINASE ACTIVITY PROBE AND METHOD OF USING

RELATED APPLICATIONS

This application claims the benefit of U.S. Provisional Patent Application No. 60/864,350 filed Nov. 3, 2006, the disclosure of which is herein incorporated in its entirety.

FIELD OF INVENTION

Described herein are probes for Bruton's tyrosine kinase (Btk) and the uses of such probes for measuring the active of Btk, for assessing the activity of modulators of Btk, and for assessing the pharmacokinetic and pharmacodynamic properties of such modulators.

BACKGROUND

Bruton's tyrosine kinase (Btk), a member of the Tec family of non-receptor tyrosine kinases, plays an essential role in the B-cell signaling pathway linking cell surface B-cell receptor (BCR) stimulation to downstream intracellular responses. It is required for the normal development and function of B-lymphocytes in humans and mice as evidenced by mutations in the Btk gene that result in the X-linked agammaglobulinemia (XLA) phenotype in humans and a less severe X-linked immunodeficiency phenotype (xid) in mice. See, e.g., D. A. Fruman, et al., (2000), *Immunity* 13:1-3. Btk is expressed in all hematopoietic cells types except T lymphocytes and natural killer cells, and participates in a number of TLR and cytokine receptor signaling pathways including lipopolysaccharide (LPS) induced TNF-α production in macrophages, suggesting a general role for Btk in immune regulation.

Btk contains an amino-terminal pleckstrin homology (PH) domain, followed by a Tec homology (TH) domain, regulatory Src homology (SH3, SH2) domains, and a C-terminal kinase (SH1) domain. In unstimulated B cells, Btk is localized to the cytoplasm where it is catalytically inactive, presumably due to a tertiary conformation arising from intramolecular interactions between the kinase domain and the SH2 and/or SH3 domains that block access of substrates to the active site. After BCR stimulation, Btk is recruited to the cell membrane via interactions between the N-terminal PH domain and cell membrane phosphoinositides. Membrane-associated Btk is then phosphorylated at Tyr 551 in the activation loop by Src family kinases. Subsequent Btk autophosphorylation at Tyr 223 stabilizes the active conformation and fully activates Btk kinase activity. Activated Btk phosphorylates phospholipase (PLCγ), initiating calcium mobilization and generating diacylglycerol (DAG) as secondary signals, eventually leading to transcriptional activation and amplification of BCR stimulation.

SUMMARY OF THE INVENTION

Described herein are activity probes of Bruton's tyrosine kinase (Btk). Further described are activity probes of Btk that include an irreversible inhibitor of Btk, a linker moiety, and a reporter moiety. Further described are activity probes of Btk that include a Michael addition acceptor moiety in the structure of the activity probe. Further described are activity probes of Btk that form a covalent bond with a cysteine residue on Btk. Also described herein are activity probes that form a non-covalent bond with a cysteine residue on Btk. Further described herein are activity probes of other tyrosine kinases, wherein the other tyrosine kinases share homology with or are substantially identical to Btk by having a cysteine residue (including a Cys 481 residue) that form a covalent or non-covalent bond with the activity probe. Also described herein are methods for synthesizing such activity probes, methods for using such activity probes in the study of the activity of Btk and other tyrosine kinases that have a Cys 481 residue, methods for using such activity probes in the study of inhibitors of Btk and other tyrosine kinases that have a Cys 481 residue, and methods for using such activity probes in the study of the pharmacodynamics of inhibitors of Btk and other tyrosine kinases that have a Cys 481 residue.

In one aspect is a Btk activity probe comprising a Btk inhibitor moiety, a reporter moiety, and a linker moiety that links the inhibitor moiety to the reporter moiety.

In one embodiment is a Btk activity probe wherein the linker moiety covalently links the inhibitor moiety to the reporter moiety. In another embodiment is a Btk activity probe wherein the Btk inhibitor moiety modifies a cysteine residue of a Btk enzyme. In a further embodiment is a Btk activity probe wherein the Btk inhibitor moiety covalently modifies the cysteine residue of the Btk enzyme. In yet a further embodiment is a Btk activity probe wherein the cysteine residue is in the ATP binding pocket of the Btk enzyme. In yet another embodiment is a Btk activity probe wherein the cysteine residue is Cys 481 of the Btk enzyme. In one embodiment is a Btk activity probe wherein the linker moiety is selected from a bond, an optionally substituted alkyl moiety, an optionally substituted heterocycle moiety, an optionally substituted amide moiety, a ketone moiety, an optionally substituted carbamate moiety, an ester moiety, or a combination thereof. In another embodiment is a Btk activity probe wherein the linker moiety comprises an optionally substituted heterocycle moiety. In a further embodiment is a Btk activity probe wherein the optionally substituted heterocycle moiety comprises a piperazinyl-based moiety.

Also described herein is a Btk activity probe wherein the reporter moiety is selected from the group consisting of a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a ligand, a photoisomerizable moiety, biotin, a biotin analogue, a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, or a combination thereof. In another embodiment is a Btk activity probe wherein the reporter moiety is a fluorophore. In yet another embodiment is a Btk activity probe wherein the fluorophore is a BODIPY® fluorophore. In yet a further embodiment is a Btk activity probe wherein the BODIPY® fluorophore is a BODIPY® FL fluorophore.

Presented herein is a Btk activity probe wherein the inhibitor moiety is derived from an irreversible inhibitor of Btk. In one embodiment, is a Btk activity probe wherein the irreversible inhibitor of Btk is:

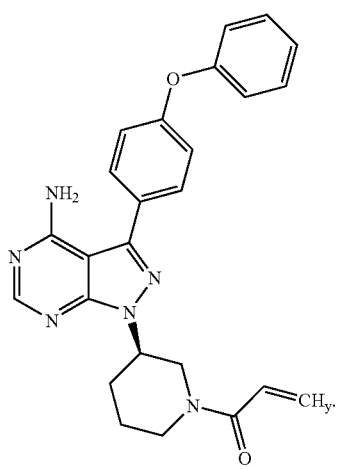

In another embodiment is a Btk activity probe having the structure:

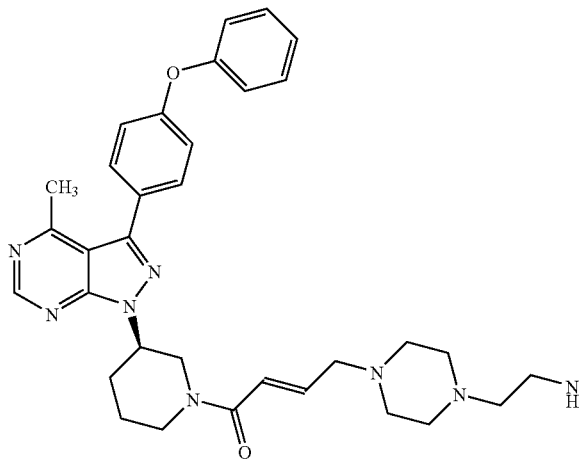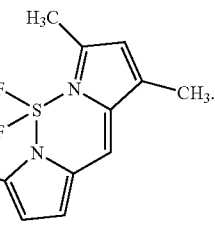

In a further embodiment is a Btk activity probe wherein the probe selectively labels a phosphorylated conformation of Btk. In another embodiment is a Btk activity probe wherein the phosphorylated conformation of Btk is either an active or inactive form of Btk. In a further embodiment is a Btk activity probe wherein the phosphorylated conformation of Btk is an active form of Btk. In one embodiment is a Btk activity probe of wherein the probe is cell permeable.

In one aspect is a method for assessing the efficacy of a potential Btk inhibitor in a mammal, comprising administering a potential Btk inhibitor to the mammal, administering the Btk activity probe described herein to the mammal or to cells isolated from the mammal; measuring the activity of the reporter moiety of the Btk activity probe, and comparing the activity of the reporter moiety to a standard.

In another aspect is a method for assessing the pharmacodynamics of a Btk inhibitor in a mammal, comprising administering a Btk inhibitor to the mammal, administering the Btk activity probe presented herein to the mammal or to cells isolated from the mammal, and measuring the activity of the reporter moiety of the Btk activity probe at different time points following the administration of the inhibitor.

In a further aspect is a method for in vitro labeling of a Btk enzyme comprising contacting an active Btk enzyme with the Btk activity probe described herein. In one embodiment is a method for in vitro labeling of a Btk enzyme wherein the contacting step comprises incubating the active Btk enzyme with the Btk activity probe presented herein.

In another aspect is a method for in vitro labeling of a Btk enzyme comprising contacting cells or tissues expressing the Btk enzyme with an Btk activity probe described herein.

In one aspect is a method for detecting a labeled Btk enzyme comprising separating proteins, the proteins comprising a Btk enzyme labeled by an Btk activity probe described herein, by electrophoresis and detecting the Btk activity probe by fluorescence.

It is to be understood that the methods and compositions described herein are not limited to the particular methodology, protocols, cell lines, constructs, and reagents described herein and in some embodiments will vary. It is also to be understood that the terminology used herein is for the purpose of describing particular embodiments only, and is not intended to limit the scope of the methods and compositions described herein, which will be limited only by the appended claims.

As used herein and in the appended claims, the singular forms "a," "an," and "the" include plural reference unless the context clearly indicates otherwise.

All publications, patent applications, and patents mentioned herein are incorporated by reference in their entirety for the purpose of describing and disclosing, for example, the constructs and methodologies that are described in the publications.

CERTAIN DEFINITIONS

The term "alkyl," by itself or as part of another molecule means, unless otherwise stated, a straight or branched chain, or cyclic hydrocarbon radical, or combination thereof. In some embodiments, the alkyl chain is fully saturated, mono- or polyunsaturated. In other embodiments, the alkyl chain includes di- and multivalent radicals, having the number of carbon atoms designated (i.e. $C_1$-$C_{10}$ means one to ten carbons). In other embodiments, examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. In a further embodiment, examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. In yet further embodiments, the term "alkyl," unless otherwise noted, includes those derivatives of alkyl defined in more detail herein, such as "heteroalkyl", "haloalkyl" and "homoalkyl".

The term "biophysical probe," as used herein, refers to probes which detect or monitor structural changes in molecules. In some embodiments, such molecules include, but are not limited to, proteins and the "biophysical probe" is used to detect or monitor interaction of proteins with other macromolecules. In other embodiments, examples of biophysical probes include, but are not limited to, spin-labels, fluorophores, and photoactivatable groups.

The term "carbonyl" as used herein refers to a group containing a moiety selected from the group consisting of —C(O)—, —S(O)—, —S(O)$_2$—, and —C(S)—, including, but not limited to, groups containing a least one ketone group, and/or at least one aldehyde group, and/or at least one ester group, and/or at least one carboxylic acid group, and/or at least one thioester group. Such carbonyl groups include ketones, aldehydes, carboxylic acids, esters, and thioesters. In some embodiments, such groups are a part of linear, branched, or cyclic molecules.

The term "chemiluminescent group," as used herein, refers to a group which emits light as a result of a chemical reaction without the addition of heat. By way of example only, luminol (5-amino-2,3-dihydro-1,4-phthalazinedione) reacts with oxidants like hydrogen peroxide ($H_2O_2$) in the presence of a base and a metal catalyst to produce an excited state product (3-aminophthalate, 3-APA).

The term "chromophore," as used herein, refers to a molecule which absorbs light of visible wavelengths, UV wavelengths or IR wavelengths.

The term "Cys 481," as used herein, refers to the cysteine found in kinases in FIG. 2(a) at the position corresponding to Cys 481 in Btk (i.e., the "C" highlighted in bold).

In other embodiments, the term "detectable label," as used herein, refers to a label which is observable using analytical techniques including, but not limited to, fluorescence, chemiluminescence, electron-spin resonance, ultraviolet/visible absorbance spectroscopy, mass spectrometry, nuclear magnetic resonance, magnetic resonance, and electrochemical methods.

The term "dye," as used herein, refers to a soluble, coloring substance which contains a chromophore.

The term "electron dense group," as used herein, refers to a group which scatters electrons when irradiated with an electron beam. Such groups include, but are not limited to, ammonium molybdate, bismuth subnitrate cadmium iodide, 99%, carbohydrazide, ferric chloride hexahydrate, hexamethylene tetramine, 98.5%, indium trichloride anhydrous, lanthanum nitrate, lead acetate trihydrate, lead citrate trihydrate, lead nitrate, periodic acid, phosphomolybdic acid, phosphotungstic acid, potassium ferricyanide, potassium ferrocyanide, ruthenium red, silver nitrate, silver proteinate (Ag Assay: 8.0-8.5%) "Strong", silver tetraphenylporphin (S-TPPS), sodium chloroaurate, sodium tungstate, thallium nitrate, thiosemicarbazide (TSC), uranyl acetate, uranyl nitrate, and vanadyl sulfate.

In other embodiments, the term "energy transfer agent," as used herein, refers to a molecule which either donates or accepts energy from another molecule. By way of example only, fluorescence resonance energy transfer (FRET) is a dipole-dipole coupling process by which the excited-state energy of a fluorescence donor molecule is non-radiatively transferred to an unexcited acceptor molecule which then fluorescently emits the donated energy at a longer wavelength.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

The term "fluorophore," as used herein, refers to a molecule which upon excitation emits photons and is thereby fluorescent.

In some embodiments, the term "label," as used herein, refers to a substance which is incorporated into a compound and is readily detected, whereby its physical distribution is detected and/or monitored.

The term "linkage," as used herein to refer to bonds or a chemical moiety formed from a chemical reaction between the functional group of a linker and another molecule. In some embodiments, such bonds include, but are not limited to, covalent linkages and non-covalent bonds, while such chemical moieties include, but are not limited to, esters, carbonates, imines, phosphate esters, hydrazones, acetals, orthoesters, peptide linkages, and oligonucleotide linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages means that the linkages are degradable in water or in aqueous solutions, including for example, blood. In other embodiments, enzymatically unstable or degradable linkages means that the linkage is degraded by one or more enzymes. By way of example only, PEG and related polymers include degradable linkages in the polymer backbone or in the linker group between the polymer backbone and one or more of the terminal functional groups of the polymer molecule. Such degradable linkages include, but are not limited to, ester linkages formed by the reaction of PEG carboxylic acids or activated PEG carboxylic acids with alcohol groups on a biologically active agent, wherein such ester groups generally hydrolyze under physiological conditions to release the biologically active agent. Other hydrolytically degradable linkages include but are not limited to carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The phrase "measuring the activity of the reporter moiety" (or a similarly worded phrase) refers to methods for quantifying (in absolute, approximate or relative terms) the reporter moiety in a system under study. In some embodiments, such methods include any methods that quantify a reporter moiety that is a dye; a photocrosslinker; a cytotoxic compound; a drug; an affinity label; a photoaffinity label; a reactive compound; an antibody or antibody fragment; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; a redox-active agent; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; and any combination of the above.

The term "moiety incorporating a heavy atom," as used herein, refers to a group which incorporates an ion of atom which is usually heavier than carbon. In some embodiments, such ions or atoms include, but are not limited to, silicon, tungsten, gold, lead, and uranium.

The term "nanoparticle," as used herein, refers to a particle which has a particle size between about 500 nm to about 1 nm.

The term "pharmaceutically acceptable," as used herein, refers to a material, including but not limited to, a salt, carrier or diluent, which does not abrogate the biological activity or properties of the compound, and is relatively nontoxic. In one embodiment, the material is administered to an individual without causing undesirable biological effects or interacting in a deleterious manner with any of the components of the composition in which it is contained.

The term "photoaffinity label," as used herein, refers to a label with a group, which, upon exposure to light, forms a linkage with a molecule for which the label has an affinity. By way of example only, in some embodiments, such a linkage is covalent or non-covalent.

The term "photocaged moiety," as used herein, refers to a group which, upon illumination at certain wavelengths, covalently or non-covalently binds other ions or molecules.

The term "photoisomerizable moiety," as used herein, refers to a group wherein upon illumination with light changes from one isomeric form to another.

The term "radioactive moiety," as used herein, refers to a group whose nuclei spontaneously give off nuclear radiation, such as alpha, beta, or gamma particles; wherein, alpha particles are helium nuclei, beta particles are electrons, and gamma particles are high energy photons.

The term "spin label," as used herein, refers to molecules which contain an atom or a group of atoms exhibiting an unpaired electron spin (i.e. a stable paramagnetic group) that in some embodiments are detected by electron spin resonance spectroscopy and in other embodiments are attached to another molecule. Such spin-label molecules include, but are not limited to, nitryl radicals and nitroxides, and in some embodiments are single spin-labels or double spin-labels.

The term "subject" as used herein, refers to an animal which is the object of treatment, observation or experiment. In one embodiment the subject is a mammal including, but not limited to, a human.

In some embodiments, the term "substituents" also referred to as "non-interfering substituents" "refers to groups which are used to replace another group on a molecule. Such groups include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_5$-$C_{12}$ aralkyl, $C_3$-$C_{12}$ cycloalkyl, $C_4$-$C_{12}$ cycloalkenyl, phenyl, substituted phenyl, toluolyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, —$(CH_2)_m$—O—($C_1$-$C_{10}$ alkyl) wherein m is from 1 to 8, aryl, substituted aryl, substituted alkoxy, fluoroalkyl, heterocyclic radical, substituted heterocyclic radical, nitroalkyl, —$NO_2$, —CN, —NRC(O)—($C_1$-$C_{10}$ alkyl), —C(O)—($C_1$-$C_{10}$ alkyl), $C_2$-$C_{10}$ alkthioalkyl, —C(O)O—($C_1$-$C_{10}$ alkyl), —OH, —$SO_2$, =S, —COOH, —$NR_2$, carbonyl, —C(O)—($C_1$-$C_{10}$ alkyl)-$CF_3$, —C(O)—$CF_3$, —C(O)$NR_2$, —($C_1$-$C_{10}$ aryl)-S—($C_6$-$C_{10}$ aryl), —C(O)—($C_6$-$C_{10}$ aryl), —$(CH_2)_m$—O—$(CH_2)_m$—O—($C_1$-$C_{10}$ alkyl) wherein each m is from 1 to 8, —C(O)$NR_2$, —C(S)$NR_2$, —$SO_2NR_2$, —NRC(O)$NR_2$, —NRC(S)$NR_2$, salts thereof, and the like. In some embodiments, each R group in the preceding list includes, but is not limited to, H, alkyl or substituted alkyl, aryl or substituted aryl, or alkaryl. Where substituent groups are specified by their conventional chemical formulas, written from left to right, they equally encompass the chemically identical substituents that would result from writing the structure from right to left; for example, —$CH_2O$— is equivalent to —$OCH_2$—.

In some embodiments, and by way of example only, substituents for alkyl and heteroalkyl radicals (including those groups referred to as alkylene, alkenyl, heteroalkylene, heteroalkenyl, alkynyl, cycloalkyl, heterocycloalkyl, cycloalkenyl, and heterocycloalkenyl) includes, but is not limited to: —OR, =O, =NR, =N—OR, —$NR_2$, —SR, -halogen, —$SiR_3$, —OC(O)R, —C(O)R, —$CO_2R$, —$CONR_2$, —OC(O)$NR_2$, —NRC(O)R, —NRC(O)$NR_2$, —NR(O)$_2R$, —NR—C($NR_2$)=NR, —S(O)R, —$S(O)_2R$, —$S(O)_2NR_2$, —$NRSO_2R$, —CN and —$NO_2$. In further embodiments, each R group in the preceding list includes, but is not limited to, hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or aralkyl groups. In some embodiments when two R groups are attached to the same nitrogen atom, they are combined with the nitrogen atom to form a 5-, 6-, or 7-membered ring. In other embodiments for example, —$NR_2$ includes, but is not be limited to, 1-pyrrolidinyl and 4-morpholinyl.

In other embodiments and by way of example, substituents for aryl and heteroaryl groups include, but are not limited to, —OR, =O, =NR, =N—OR, —$NR_2$, —SR, -halogen, —$SiR_3$, —OC(O)R, —C(O)R, —$CO_2R$, —$CONR_2$, —OC(O)$NR_2$, —NRC(O)R, —NRC(O)$NR_2$, —NR(O)$_2R$, —NR—C($NR_2$)=NR, —S(O)R, —$S(O)_2R$, —$S(O)_2NR_2$, —$NRSO_2R$, —CN, —$NO_2$, —R, —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system. In a further embodiment, each R group in the preceding list includes, but is not limited to, hydrogen, alkyl, heteroalkyl, aryl and heteroaryl.

Unless otherwise indicated, conventional methods of mass spectroscopy, NMR, HPLC, protein chemistry, biochemistry, recombinant DNA techniques and pharmacology, are employed.

Compounds presented herein include isotopically-labeled compounds, which are identical to those recited in the various formulas and structures presented herein, but for the fact that one or more atoms are replaced by an atom having an atomic mass or mass number different from the atomic mass or mass number usually found in nature. In some embodiments examples of isotopes that are incorporated into the present compounds include isotopes of hydrogen, carbon, nitrogen, oxygen, fluorine and chlorine, such as $^2H$, $^3H$, $^{13}C$, $^{14}C$, $^{15}N$, $^{18}O$, $^{17}O$, $^{35}S$, $^{18}F$, $^{36}Cl$, respectively. Certain isotopically-labeled compounds described herein, for example those into which radioactive isotopes such as $^3H$ and $^{14}C$ are incorporated, are useful in drug and/or substrate tissue distribution assays. Further, in other embodiments, substitution with isotopes such as deuterium, i.e., $^2H$, affords certain therapeutic advantages resulting from greater metabolic stability, for example increased in vivo half-life or reduced dosage requirements.

In other embodiments, are compounds described herein having asymmetric carbon atoms and therefore exist as enantiomers or diastereomers. In some embodiments, diastereomeric mixtures are separated into their individual diastereomers on the basis of their physical chemical differences, for example, by chromatography and/or fractional crystallization. In other embodiments enantiomers are separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

In additional or further embodiments, the compounds described herein are used in the form of pro-drugs. In additional or further embodiments, the compounds described herein are metabolized upon administration to an organism in need to produce a metabolite that is then used to produce a desired effect, including a desired therapeutic effect.

The methods and formulations described herein include the use of N-oxides, crystalline forms (also known as polymorphs), or pharmaceutically acceptable salts. In certain embodiments, compounds described herein exist as tautomers. All tautomers are included within the scope of the compounds presented herein. In some embodiments, the compounds described herein exist in unsolvated as well as solvated forms with pharmaceutically acceptable solvents such as water, ethanol, and the like. The solvated forms of the compounds presented herein are also considered to be disclosed herein.

In further embodiments are compounds described herein which exist in several tautomeric forms. All such tautomeric forms are considered as part of the compositions described herein. Also, for example in some embodiments, all enol-keto forms of any compounds herein are considered as part of the compositions described herein.

In other embodiments, are compounds described herein are acidic and in some embodiments form a salt with a pharmaceutically acceptable cation. Some of the compounds herein are basic and in some embodiments, form a salt with a pharmaceutically acceptable anion. All such salts, including di-salts are within the scope of the compositions described herein and in some embodiments are prepared by conventional methods. For example, in other embodiments salts are prepared by contacting the acidic and basic entities, in either an aqueous, non-aqueous or partially aqueous medium. The salts are recovered by using at least one of the following techniques: filtration, precipitation with a non-solvent followed by filtration, evaporation of the solvent, or, in the case of aqueous solutions, lyophilization.

In some embodiments, pharmaceutically acceptable salts of the compounds disclosed herein are formed when an acidic proton present in the parent compound either is replaced by a metal ion, by way of example an alkali metal ion, an alkaline earth ion, or an aluminum ion; or coordinates with an organic base. In addition, in other embodiments, the salt forms of the disclosed compounds are prepared using salts of the starting materials or intermediates.

In further embodiments, the type of pharmaceutical acceptable salts, include, but are not limited to: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion, an alkaline earth ion, or an aluminum ion; or coordinates with an organic base. In yet a further embodiment, acceptable organic bases include ethanolamine, diethanolamine, triethanolamine, tromethamine, N-methylglucamine, and the like. In some embodiments, acceptable inorganic bases include aluminum hydroxide, calcium hydroxide, potassium hydroxide, sodium carbonate, sodium hydroxide, and the like.

In some embodiments, the corresponding counter-ions of the pharmaceutically acceptable salts are analyzed and identified using various methods including, but not limited to, ion exchange chromatography, ion chromatography, capillary electrophoresis, inductively coupled plasma, atomic absorption spectroscopy, mass spectrometry, or any combination thereof.

It should be understood that in some embodiments, a reference to a salt includes the solvent addition forms or crystal forms thereof, particularly solvates or polymorphs. In further embodiments, solvates contain either stoichiometric or non-stoichiometric amounts of a solvent, and are often formed during the process of crystallization with pharmaceutically acceptable solvents such as water, ethanol, and the like. In yet another embodiment, hydrates are formed when the solvent is water, or alcoholates are formed when the solvent is alcohol. Polymorphs include the different crystal packing arrangements of the same elemental composition of a compound. In one embodiment, are polymorphs having different X-ray diffraction patterns, infrared spectra, melting points, density, hardness, crystal shape, optical and electrical properties, stability, and solubility. In further embodiments, various factors such as the recrystallization solvent, rate of crystallization, and storage temperature cause a single crystal form to dominate.

In other embodiments, the screening and characterization of the pharmaceutically acceptable salts, polymorphs and/or solvates is accomplished using a variety of techniques including, but not limited to, thermal analysis, x-ray diffraction, spectroscopy, vapor sorption, and microscopy. In yet a further embodiment, thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning Calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UVIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

BRIEF DESCRIPTION OF THE DRAWINGS

A better understanding of the features and advantages of the present methods and compositions are obtained by reference to the following detailed description that sets forth illustrative embodiments, in which the principles of our methods, compositions, devices and apparatuses are utilized, and the accompanying drawings of which.

DETAILED DESCRIPTION OF THE INVENTION

Figure 1:
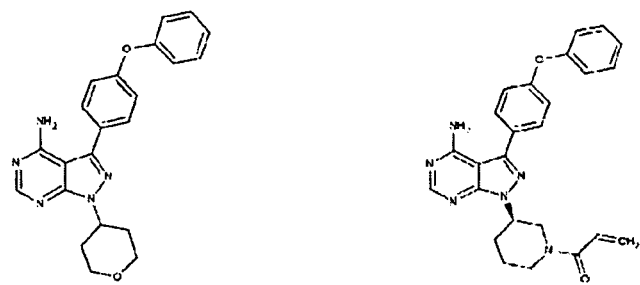
FIG. 1 presents structures of reversible (Compound 1) and irreversible (Compound 2) Btk inhibitors and an illustrative Btk kinase probe derived from Compound 2 (Compound 3) and an illustrative probe derived from Compound 2 that is not a Btk probe (Compound 4).
Figure 1:
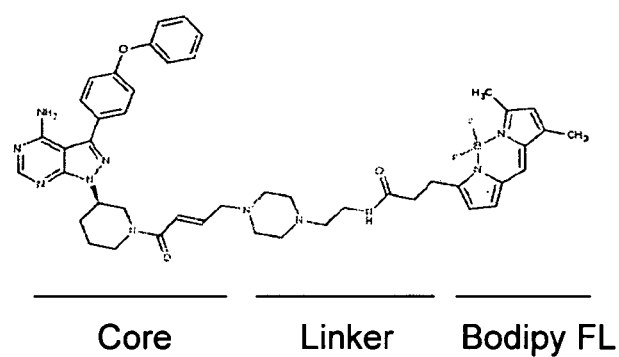
Figure 1:
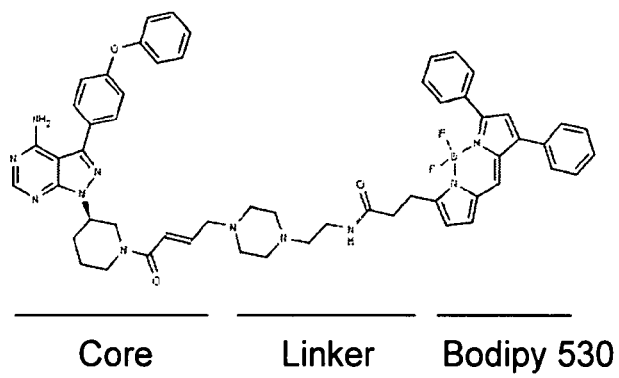

Disclosed herein is the synthesis and characterization of cell permeable probes that label Btk at a unique, non-catalytic cysteine residue in the ATP binding pocket. Other embodiments disclosed herein demonstrate the utility of such probes in assessing pharmacodynamics in mammals treated with small molecule Btk inhibitors.

Btk Activity Probe Compounds

The Btk activity probe compounds described herein are composed of a moiety comprising an inhibitor of Btk, a linker moiety, and a reporter moiety. In one embodiment, the inhibitor of Btk is an irreversible inhibitor. In another embodiment, the irreversible inhibitor of Btk binds to a non-catalytic residue in the ATP binding pocket of Btk; in further embodiments, the non-catalytic residue is a cysteine residue. In some embodiments, the Btk activity probe forms a covalent bond with at least one non-catalytic residue of Btk. In other embodiments, the Btk activity probe forms a non-covalent bond with at least one non-catalytic residue of Btk. In a further embodiment, the Btk activity probe forms hydrogen bonding within the ATP binding pocket of Btk. In yet a further embodiment, the Btk activity probe has Van der Waals attractions with the Btk enzyme.

In some other embodiments, the Btk activity probes described herein are activity dependent such that the probe binds only an active Btk enzyme. In further embodiments, the Btk activity probe binds a Btk enzyme that has been switched on by phosphorylation by upstream kinases. In yet a further embodiment, the Btk activity probes described herein are activity independent such that the probe binds Btk enzymes that have not been switched on by phosphorylation by upstream kinases. In some embodiments, the Btk activity probe labels a phosphorylated conformation of a Btk enzyme. In other embodiments, the Btk activity probe labels a Btk in a non-phosphorylated conformation.

In some embodiments, the Btk activity probe is permeable to cells.

In further embodiments, the linker moiety is selected from a bond, a substituted alkyl moiety, a substituted heterocycle moiety, a substituted amide moiety, a ketone moiety, a substituted carbamate moiety, an ester moiety, or any combination thereof. In further embodiments, the reporter moiety is a moiety that is detected using standard or modified laboratory equipment.

Compounds and methods for Btk inhibition are discussed throughout.

In one aspect is a Btk activity probe of Formula (I) comprising:

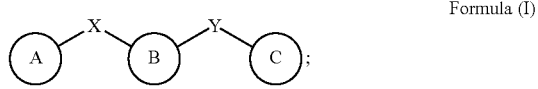

Formula (I)

wherein:
A is a Btk inhibitor moiety;
X and Y are independently selected from the group consisting of: a bond, —O(C=O)—, —NR$^a$(C=O)—, —NR$^a$—,

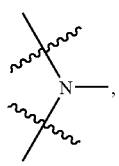

—O—, —S—, —S—S—, —O—NR$^a$—, —O(C=O)O—, —O(C=O)NR$^a$, —NR$^a$(C=O)NR$^a$, N=CR$^a$—, —S(C=O)—, —S(O)—, and —S(O)$_2$—;
wherein

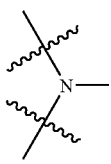 [SMILES: *N(*)C]

forms a N-containing heterocycle;
B is a linker moiety;
C is a reporter moiety; and
R$^a$ is hydrogen or alkyl.

In one embodiment, the moiety comprising an irreversible inhibitor of Btk is derived from an irreversible inhibitor of Btk. In some embodiments, such irreversible inhibitors of Btk should possess at least one of the following characteristics: potency, selectively and cell permeability. In further embodiments, such irreversible inhibitors of Btk possess at least two of the aforementioned characteristics, and in further embodiments, at least all of the aforementioned characteristics.

In another embodiment, the Btk inhibitor moiety is derived from a Btk inhibitor having the structure of Formula (II):

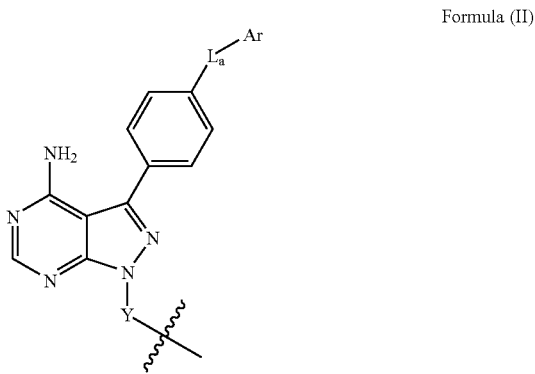

Formula (II)

wherein:
L$_a$ is CH$_2$, O, NH or S;
Ar is a substituted or unsubstituted aryl, or a substituted or unsubstituted heteroaryl; and
Y is an optionally substituted group selected from among alkyl, heteroalkyl, cycloalkyl, heterocycloalkyl, aryl, and heteroaryl.

In some embodiments, L$_a$ is CH$_2$, O, or NH. In other embodiments, L$_a$ is O or NH. In yet other embodiments, L$_a$ is O.

In other embodiments, Ar is a substituted or unsubstituted aryl. In yet other embodiments, Ar is a 6-membered aryl. In some other embodiments, Ar is phenyl.

In some embodiments, Y is an optionally substituted group selected from among alkyl, heteroalkyl, cycloalkyl, and heterocycloalkyl. In other embodiments, Y is an optionally substituted group selected from among $C_1$-$C_6$alkyl, $C_1$-$C_6$heteroalkyl, 4-, 5-, 6-, or 7-membered cycloalkyl, and 4-, 5-, 6-, or 7-membered heterocycloalkyl. In yet other embodiments, Y is an optionally substituted group selected from among $C_1$-$C_6$alkyl, $C_1$-$C_6$heteroalkyl, 5- or 6-membered cycloalkyl, and 5- or 6-membered heterocycloalkyl containing 1 or 2 N atoms. In some other embodiments, Y is a 5- or 6-membered cycloalkyl, or a 5- or 6-membered heterocycloalkyl containing 1 or 2 N atoms. In some embodiments, Y is a 4-, 5-, 6-, or 7-membered cycloalkyl ring; or Y is a 4-, 5-, 6-, or 7-membered heterocycloalkyl ring.

In some embodiments, the Btk inhibitor moiety is derived from a compound selected from among: 1-(3-(4-amino-3-(4-phenoxyphenyl)-1H-pyrazolo[3,4-d]pyrimidin-1-yl)piperidin-1-yl)prop-2-en-1-one; (E)-1-(3-(4-amino-3-(4-phenoxyphenyl)-1H-pyrazolo[3,4-d]pyrimidin-1-yl)piperidin-1-yl)but-2-en-1-one; 1-(3-(4-amino-3-(4-phenoxyphenyl)-1H-pyrazolo[3,4-d]pyrimidin-1-yl)piperidin-1-yl) sulfonylethene; 1-(3-(4-amino-3-(4-phenoxyphenyl)-1H-pyrazolo[3,4-d]pyrimidin-1-yl)piperidin-1-yl)prop-2-yn-1-one; 1-(4-(4-amino-3-(4-phenoxyphenyl)-1H-pyrazolo[3,4-d]pyrimidin-1-yl)piperidin-1-yl)prop-2-en-1-one; N-((1s,4s)-4-(4-amino-3-(4-phenoxyphenyl)-1H-pyrazolo[3,4-d]pyrimidin-1-yl)cyclohexyl)acrylamide; 1-((R)-3-(4-amino-3-(4-phenoxyphenyl)-1H-pyrazolo[3,4-d]pyrimidin-1-yl)pyrrolidin-1-yl)prop-2-en-1-one; 1-((S)-3-(4-amino-3-(4-phenoxyphenyl)-1H-pyrazolo[3,4-d]pyrimidin-1-yl)pyrrolidin-1-yl)prop-2-en-1-one; 1-((R)-3-(4-amino-3-(4-phenoxyphenyl)-1H-pyrazolo[3,4-d]pyrimidin-1-yl)piperidin-1-yl)prop-2-en-1-one; 1-((S)-3-(4-amino-3-(4-phenoxyphenyl)-1H-pyrazolo[3,4-d]pyrimidin-1-yl)piperidin-1-yl)prop-2-en-1-one; and (E)-1-(3-(4-amino-3-(4-phenoxyphenyl)-1H-pyrazolo[3,4-d]pyrimidin-1-yl)piperidin-1-yl)-4-(dimethylamino)but-2-en-1-one.

In another embodiment, the linker moiety is selected from a bond, a polymer, a water soluble polymer, optionally substituted alkyl, optionally substituted heteroalkyl, optionally substituted heterocycloalkyl, optionally substituted cycloalkyl, optionally substituted heterocycloalkylalkyl, optionally substituted heterocycloalkylalkenyl, optionally substituted aryl, optionally substituted heteroaryl, and optionally substituted heterocycloalkylalkenylalkyl. In some embodiments, the linker moiety is an optionally substituted heterocycle. In other embodiments, the heterocycle is selected from aziridine, oxirane, episulfide, azetidine, oxetane, pyrroline, tetrahydrofuran, tetrahydrothiophene, pyrrolidine, pyrazole, pyrrole, imidazole, triazole, tetrazole, oxazole, isoxazole, oxirene, thiazole, isothiazole, dithiolane, furan, thiophene, piperidine, tetrahydropyran, thiane, pyridine, pyran, thiapyrane, pyridazine, pyrimidine, pyrazine, piperazine, oxazine, thiazine, dithiane, and dioxane. In some embodiments, the heterocycle is piperazine. In further embodiments, the linker moiety is optionally substituted with halogen, CN, OH, $NO_2$, alkyl, S(O), and $S(O)_2$. In other embodiments, the water soluble polymer is a PEG group.

In other embodiments, the linker moiety provides sufficient spatial separation between the reporter moiety and the Btk inhibitor moiety. In further embodiments, the linker moiety is stable. In yet a further embodiment, the linker moiety does not substantially affect the response of the reporter moiety. In other embodiments the linker moiety provides chemical stability to the Btk activity probe. In further embodiments, the linker moiety provides sufficient solubility to the Btk activity probe.

In some embodiments, linkages such as water soluble polymers are coupled at one end to a Btk inhibitor moiety and to a reporter moiety at the other end. In other embodiments, the water soluble polymers are coupled via a functional group or substituent of the Btk inhibitor moiety. In further embodiments, the water soluble polymers are coupled via a functional group or substituent of the reporter moiety. In other embodiments, covalent attachment of hydrophilic polymers to a Btk inhibitor moiety and a reporter moiety represents one approach to increasing water solubility (such as in a physiological environment), bioavailability, increasing serum half-life, increasing pharmacodynamic parameters, or extending the circulation time of the Btk activity probe, including proteins, peptides, and particularly hydrophobic molecules. In further embodiments, additional important features of such hydrophilic polymers include biocompatibility and lack of toxicity. In other embodiments, for therapeutic use of the end-product preparation, the polymer is pharmaceutically acceptable.

In some embodiments, examples of hydrophilic polymers include, but are not limited to: polyalkyl ethers and alkoxy-capped analogs thereof (e.g., polyoxyethylene glycol, polyoxyethylene/propylene glycol, and methoxy or ethoxy-capped analogs thereof, polyoxyethylene glycol, the latter is also known as polyethylene glycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof, hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof, terpolymers thereof, mixtures thereof, and derivatives of the foregoing. In other embodiments, the water soluble polymer is any structural form including but not limited to linear, forked or branched. In some embodiments, polymer backbones that are water-soluble, with from 2 to about 300 termini, are particularly useful. In further embodiments, multifunctional polymer derivatives include, but are not limited to, linear polymers having two termini, each terminus being bonded to a functional group which is the same or different. In some embodiments, the water polymer comprises a poly(ethylene glycol) moiety. In further embodiments, the molecular weight of the polymer is of a wide range, including but not limited to, between about 100 Da and about 100,000 Da or more. In yet further embodiments, the molecular weight of the polymer is between about 100 Da and about 100,000 Da, including but not limited to, about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, about 1,000 Da, about 900

Da, about 800 Da, about 700 Da, about 600 Da, about 500 Da, about 400 Da, about 300 Da, about 200 Da, and about 100 Da. In some embodiments, the molecular weight of the polymer is between about 100 Da and 50,000 Da. In some embodiments, the molecular weight of the polymer is between about 100 Da and 40,000 Da. In some embodiments, the molecular weight of the polymer is between about 1,000 Da and 40,000 Da. In some embodiments, the molecular weight of the polymer is between about 5,000 Da and 40,000 Da. In some embodiments, the molecular weight of the polymer is between about 10,000 Da and 40,000 Da. In some embodiments, the poly (ethylene glycol) molecule is a branched polymer. In further embodiments, the molecular weight of the branched chain PEG is between about 1,000 Da and about 100,000 Da, including but not limited to, about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, about 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, and about 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da. The foregoing list for substantially water soluble backbones is by no means exhaustive and is merely illustrative, and in some embodiments, the polymeric materials having the qualities described above suitable for use in methods and compositions described herein.

In further embodiments, the number of water soluble polymers linked to a Btk inhibitor moiety and a reporter moiety described herein is adjusted to provide an altered (including but not limited to, increased or decreased) pharmacologic, pharmacokinetic or pharmacodynamic characteristic such as in vivo half-life. In some embodiments, the half-life of the Btk activity probe is increased at least about 10, about 20, about 30, about 40, about 50, about 60, about 70, about 80, about 90 percent, about two fold, about five-fold, about 10-fold, about 50-fold, or at least about 100-fold over a Btk activity probe without a water soluble linker.

In another embodiment, X is selected from the group consisting of: a bond, —O(C=O)—, —NR$^a$(C=O)—, —NR$^a$—,

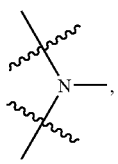 [SMILES: *N(*)C ; ","]

—O—, —S—, —S—S—, —O—NR$^a$—, —O(C=O)O—, —O(C=O)NR$^a$, —NR$^a$(C=O)NR$^a$—, —N=CR$^a$—, —S(C=O)—, —S(O)—, and —S(O)$_2$—;

wherein

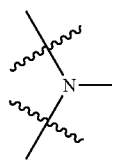 [SMILES: *N(*)C]

forms a N-containing heterocycle. In one embodiment, X is NR$^a$(C=O). In another embodiment, X is a bond. In another embodiment, X is —O(C=O)—. In a further embodiment, Y is selected from the group consisting of: a bond, —O(C=O)—, —NR$^a$(C=O)—, —NR$^a$—,

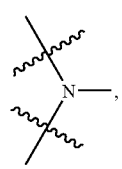 [SMILES: *N(*)C ; ","]

—O—, —S—, —S—S—, —O—NR$^a$—, —O(C=O)O—, —O(C=O)NR$^a$, —NR$^a$(C=O)NR$^a$—, —N=CR$^a$—, —S(C=O)—, —S(O)—, and —S(O)$_2$—;

wherein

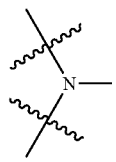 [SMILES: *N(*)C]

forms a N-containing heterocycle. In yet a further embodiment, Y is a bond. In one embodiment, Y is —NR$^a$(C=O)—. In yet another embodiment, R$^a$ is hydrogen. In yet a further embodiment, R$^a$ is alkyl.

In a further embodiment, the reporter moiety is selected from the group consisting of a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a ligand, a photoisomerizable moiety, biotin, a biotin analog, a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, or a combination thereof.

In another embodiment, the reporter moiety is a fluorophore. In a further embodiment, the fluorophore is selected from the group consisting of: BODIPY® 493/503, BODIPY® FL, BODIPY® R6G, BODIPY® 530/550, BODIPY® TMR, BODIPY® 558/568, BODIPY® 564/570, BODIPY® 576/589, BODIPY® 581/591, BODIPY® TR, Fluorescein, 5(6)-Carboxyfluorescein, 2,7-Dichlorofluorescein, N,N-Bis(2,4,6-trimethylphenyl)-3,4:9,10-perylenebis (dicarboximide, HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, BCECF, dichlorofluorescein, rhodamine 110, rhodamine 123, Rhodamine Green, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, Diversa Green-FP, Dragon Green, EvaGreen, Surf Green EX, Spectrum Green, Oregon Green 488, NeuroTrace 500525, NBD-X, MitoTracker Green FM, LysoTracker Green DND-26, CBQCA, PA-GFP (post-activation), WEGFP (post-activation), FlASH-CCXXCC, Azami Green monomeric, Azami Green, EGFP (Campbell Tsien 2003), EGFP (Patterson 2001), Fluorescein, Kaede Green, 7-Benzylamino-4-Nitrobenz-2-Oxa-1,3-Diazole, Bex1, Doxorubicin, Lumio Green, and SuperGlo GFP.

In a further embodiment, the fluorophore is selected from the group consisting of: BODIPY® 493/503 (4,4-difluoro-1,3,5,7,8-pentamethyl-4-bora-3a,4a-diaza-s-indacene), BODIPY® FL (4,4-difluoro-5,7-dimethyl-4-bora-3a,4a-diaza-s-indacene-3-propionic acid), BODIPY® R6G (4,4-difluoro-5-phenyl-4-bora-3a,4a-diaza-s-indacene-3-propionic acid), BODIPY® 530/550 (4,4-difluoro-5,7-diphenyl-4-bora-3a,4a-diaza-s-indacene-3-propionic acid), BODIPY® TMR, BODIPY® 558/568 (4,4-difluoro-5-(2-thienyl)-4-bora-3a,4a-diaza-s-indacene-3-propionic acid), BODIPY® 564/570 (4,4-difluoro-5-styryl-4-bora-3a,4a-diaza-s-indacene-3-propionic acid), BODIPY® 576/589 (4,4-difluoro-5-(2-pyrrolyl)-4-bora-3a,4a-diaza-s-indacene-3-propionic acid), BODIPY® 581/591 (4,4-difluoro-5-(4-phenyl-1,3-butadienyl)-4-bora-3a,4a-diaza-s-indacene-3-propionic acid), and BODIPY® TR(6-(((4-(4,4-difluoro-5-(2-thienyl)-4-bora-3a,4a-diaza-s-indacene-3-yl)phenoxy)acetyl)amino)hexanoic acid). In yet a further embodiment, the fluorophore is BODIPY® FL. In certain embodiments, the fluorophore is not BODIPY® 530. In some embodiments, the fluorophore has an excitation maxima of between about 500 and about 600 nm. In some other embodiments, the fluorophore has an excitation maxima of between about 500 and about 550 nm. In another embodiments, the fluorophore has an excitation maxima of between about 550 and about 600 nm. In yet a further embodiment, the fluorophore has an excitation maxima of between about 525 and about 575 nm. In other embodiments, the fluorophore has an emission maxima of between about 510 and about 670 nm. In another embodiment, the fluorophore has an emission maxima of between about 510 and about 600 nm. In a further embodiment, the fluorophore has an emission maxima of between about 600 and about 670 nm. In another embodiment, the fluorophore has an emission maxima of between about 575 and about 625 nm.

By way of example only and in some embodiments, the observed potency, selectivity, and cell permeability of compounds such as Compound 2 are appropriate to incorporate these molecules into a Btk-targeted, activity based probe that allows direct visualization of Btk activity in intact cells. In vitro profiling against a panel of greater than 100 kinases showed Compound 2 to be a highly potent and selective inhibitor of Tec family kinases, including, Btk, as well as Src family kinases. Without limiting the scope of the compositions and methods described herein, it is postulated that the structural basis for the selectivity is covalent modification of a non-catalytic cysteine residue (Cys 481 in Btk) that is conserved in the ATP binding pocket of the Tec family and several other kinases (FIG. 2a). Compound 2 inhibited Btk activity in cell-based assays and was efficacious in a mouse model of rheumatoid arthritis (Table 1). Compound 2 (FIG. 1) is an illustrative irreversible inhibitor of Btk with an $IC_{50}$ equal to 0.5 nM. Compound 1 is an illustrative structurally-related, reversible Btk inhibitor used in competition experiments as described below.

TABLE 1

Inhibition profiles for Compounds 1-3 in selected kinase assays and in a cell based calcium mobilization assay ($Ca^{2+}$ flux).
Data are $IC_{50}$ values in µM.

|  | Compound 1 | Compound 2 | Compound 3 (probe) |
|---|---|---|---|
| Abl | 0.81 | 0.78 | 0.3 |
| Btk | 0.031 | 0.0005 | 0.089 |
| c-met | 82 | 35 | 100 |
| EGFR | — | — | 2.9 |
| Lck | 0.01 | 0.12 | 0.24 |
| $Ca^{2+}$ flux | 0.62 | 0.01 | 0.23 |

However, in other embodiments, any irreversible inhibitor of Btk that binds to the non-catalytic cysteine residue in the ATP binding pocket of Btk is used in the compounds and methods described herein.

General Synthesis and Characterization of an Illustrative Btk Activity Probe

Figures 2A, 2B:
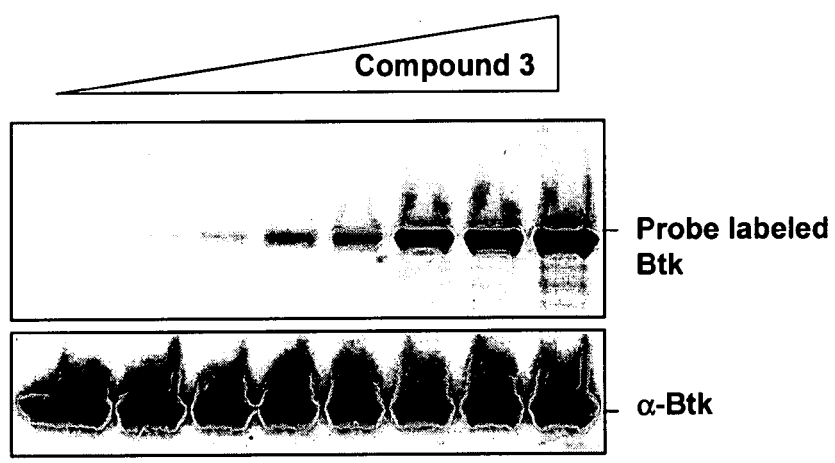
FIG. 2 presents characterization of an illustrative Btk probe (Compound 3) in vitro. (a) Sequence alignments of the ATP binding pocket in kinases containing the conserved cysteine (arrow) corresponding to Cys 481 in Btk. The protein accession numbers are also shown (SEQ ID NOS 3-12 are disclosed respectively in order of appearance). (b) Dose-dependent labeling of purified, active Btk in vitro. A fixed amount of Btk enzyme (1 µg, yielding 0.13 uM final concentration) was incubated with 0-10 µM probe in 3-fold increments (left to right: 0 µM, 0.007 µM, 0.024 µM, 0.08 µM, 0.27 µM, 0.9 µM, 3 µM, 10 µM). The lower panel shows equal loading of Btk in each lane as detected by anti-Btk western blotting of the same gel. (c) Competition for labeling of Btk following pre-incubation of Btk with 1 µM Compound 2 (lane 1) or 0.5 mM ATPγS (lane 3). Lane 2 and lane 4 are from probe labeling of Btk without competitor. (d) Incubation of active, recombinant His6-Btk (6×His tag disclosed as SEQ ID NO: 2) with (+CIP) or without (−CIP) calf intestinal alkaline phosphatase followed by labeling with 1 µM probe and analysis by SDS-PAGE (top panel). The middle and bottom panels show the anti-Btk and anti-phosphotyrosine (4G10) immunoblots of the same gel, respectively.

Without limiting the scope of the compositions described herein, an illustrative probe (Compound 3) was synthesized by attaching a bodipy FL fluorophore to Compound 2 via a piperazine linker (FIG. 1). The piperazine linker served to maintain probe solubility and provided spatial separation between the fluorophore and the pyrazolopyrimidine core.

In some embodiments, the linkage formed is a stable linkage. In other embodiments, in the case where the conjugate comprises two components, the linker moiety forms a linkage, in some embodiments, a stable linkage, between the inhibitor moiety and the reporter moiety. In some embodiments, the linker moiety is stable and provides the means to control and determine the distance between the inhibitor moiety and the report moiety. Further, in some embodiments, the linker moiety is selected such that the probe's solubility is maintained. In some embodiments, the linker moiety is a piperazinyl moiety. In further embodiments, a piperazinyl-based linkage is formed by using a piperazine containing compound. In other embodiments, the number and order of units that comprise the linker moiety is selected such that the length between the first component and the second component, as well as the hydrophobic and hydrophilic characteristics of the linker is controlled.

In the present context, spatial separation means a thermochemically and photochemically non-active distance-making group and in some embodiments is used to join two or more different moieties of the types defined above. In other embodiments, spacers are selected on the basis of a variety of characteristics including their hydrophobicity, hydrophilicity, molecular flexibility and length. The spacer, thus, in some embodiments, comprises a chain of carbon atoms optionally interrupted or terminated with one or more heteroatoms, such as oxygen atoms, nitrogen atoms, and/or sulphur atoms. Thus, in some embodiments, the spacer comprises one or more amide, ester, amino, ether, and/or thioether functionalities, and optionally aromatic or mono/polyunsaturated hydrocarbons, polyoxyethylene such as polyethylene glycol, oligo/polyamides such as poly-.α-alanine, polyglycine, polylysine, and peptides in general, oligosaccharides, oligo/polyphosphates. Moreover, in other embodiments, the spacer consists of combined units thereof. In further embodiments, the length of the spacer varies, taking into consideration the desired or necessary positioning and spatial orientation of the active/functional part of the Btk activity probe.

Without limiting the scope of the compositions described herein, in some embodiments the reporter moiety is Bodipy. In the present context, the term reporter moiety means a group which is detectable either by itself or as a part of a detection series.

In some embodiments, Compound 3 retains the solubility and membrane permeability of Compound 2, allowing detection and quantitation of labeled Btk by SDS-PAGE and laser densitometry.

In some embodiments, the labeled Btk activity probes described herein are purified by one or more procedures including, but are not limited to, affinity chromatography; anion- or cation-exchange chromatography (using, including but not limited to, DEAE SEPHAROSE®); chromatography on silica; reverse phase HPLC; gel filtration (using, including but not limited to, SEPHADEX® G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), or extraction. In other embodiments, apparent molecular weight is estimated by GPC by comparison to globular protein standards (PROTEIN PURIFICATION METHODS, A PRACTICAL APPROACH (Harris & Angal, Eds.) IRL Press 1989, 293-306).

In addition, in some embodiments, the synthetic procedures disclosed below includes various purifications, such as column chromatography, flash chromatography, thin-layer chromatography (TLC), recrystallization, distillation, high-pressure liquid chromatography (HPLC) and the like. Also, in other embodiments, various techniques for the identification and quantification of chemical reaction products, such as proton and carbon-13 nuclear magnetic resonance ($^1$H and $^{13}$C NMR), infrared and ultraviolet spectroscopy (IR and UV), X-ray crystallography, elemental analysis (EA), HPLC and mass spectroscopy (MS) are used as well.

Unless otherwise indicated, in some embodiments, methods of mass spectroscopy, NMR, HPLC, protein chemistry, biochemistry, recombinant DNA techniques and pharmacology are employed.

In one aspect, the in vitro inhibitory potency of a probe against a panel of selected kinases as a rapid means of confirming accessibility of the reactive moiety to the Btk active site is tested. By way of example only, although less potent than the parent Compound 2, the illustrative probe of Compound 3 retains potency against Btk ($IC_{50}$ 90 nM) (Table 1). Thus, the piperazine linker and bodipy fluorophore do not seriously compromise accessibility of the illustrative probe to the enzyme active site.

Synthesis of Compound 3—Btk Activity Probe

4-Amino-3-(4-phenoxyphenyl)-1H-pyrazolo[3,4-d]pyrimidine (Intermediate 2) is prepared. Briefly, 4-phenoxybenzoic acid (48 g) is added to thionyl chloride (100 mL) and heated under gentle reflux for 1 hour. Thionyl chloride was removed by distillation, the residual oil was dissolved in toluene and volatile material removed at 80° C./20 mbar. The resulting acid chloride was dissolved in toluene (200 mL) and tetrahydrofuran (35 mL). Malononitrile (14.8 g) was added and the solution stirred at −10° C. while adding diisopropylethylethylamine (57.9 g) in toluene (150 mL), while maintaining the temperature below 0° C. After 1 hour at 0° C., the mixture was stirred at 20° C. overnight. Amine hydrochloride is removed by filtration and the filtrate evaporated in vacuo. The residue was taken up in ethyl acetate and washed with 1.25 M sulphuric acid, then with brine and dried over sodium sulfate. Evaporation of the solvents gave a semisolid residue which was treated with a portion of ethyl acetate to give 4.1 g of 1,1-dicyano-2-hydroxy-2-(4-phenoxyphenyl)ethene as a white solid (m.p. 160-162° C.). The filtrate on evaporation gave 56.58 (96%) of 1,1-dicyano-2-hydroxy-2-(4-phenoxyphenyl)ethene as a grey-brown solid, which was sufficiently pure for further use.

1,1-Dicyano-2-hydroxy-2-(4-phenoxyphenyl)ethene (56.5 g) in acetonitrile (780 mL) and methanol (85 mL) is stirred under nitrogen at 0° C. while adding diisopropylethylamine (52.5 mL) followed by 2M trimethylsilyldiazomethane (150 mL) in THF. The reaction is stirred for 2 days at 20° C., and then 2 g of silica is added (for chromatography). The brown-red solution is evaporated in vacuo, the residue dissolved in ethyl acetate and washed well with water then brine, dried and evaporated. The residue is extracted with diethyl ether (3×250 mL), decanting from insoluble oil. Evaporation of the ether extracts gives 22.5 g of 1,1-dicyano-2-methoxy-2-(4-phenoxyphenyl)ethene as a pale orange solid. The insoluble oil is purified by flash chromatography to give 15.0 g of a red-orange oil.

1,1-Dicyano-2-methoxy-2-(4-phenoxyphenyl)ethene (22.5 g) and 1,1-dicyano-2-methoxy-2-(4-phenoxyphenyl)ethene oil (15 g) are treated with a solution of hydrazine hydrate (18 mL) in ethanol (25 mL) and heated on the steambath for 1 hour. Ethanol (15 mL) is added followed by water (10 mL). The precipitated solid is collected and washed with ethanol:water (4:1) and then dried in air to give 3-amino-4-cyano-5-(4-phenoxyphenyl)pyrazole as a pale orange solid.

3-Amino-4-cyano-5-(4-phenoxyphenyl)pyrazole (29.5 g) is suspended in formamide (300 mL) and heated under nitrogen at 180° C. for 4 hours. The reaction mixture is cooled to 30° C. and water (300 mL) is added. The solid is collected, washed well with water, then with methanol and dried in air to give of 4-amino-3-(4-phenoxyphenyl)-1H-pyrazolo[3,4-d]pyrimidine (Intermediate 2).

Synthesis of 1-(3-(4-amino-3-(4-phenoxyphenyl)-1H-pyrazolo[3,4-d]pyrimidin-1-yl)piperidin-1-yl (Intermediate 4); a) triphenylphosphine (TPP), diisopropyl diazodicarboxylate (DIAD), tetrahydrofuran (THF); b) TFA/CH$_2$Cl$_2$.

Scheme 1:

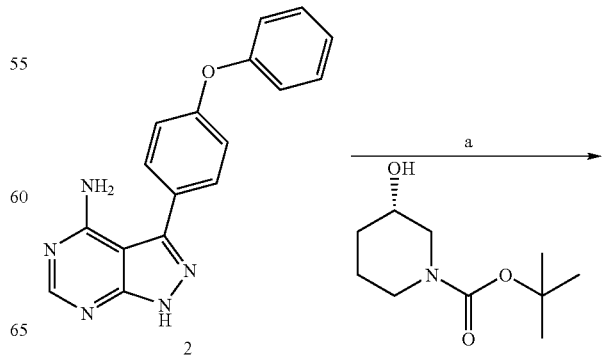

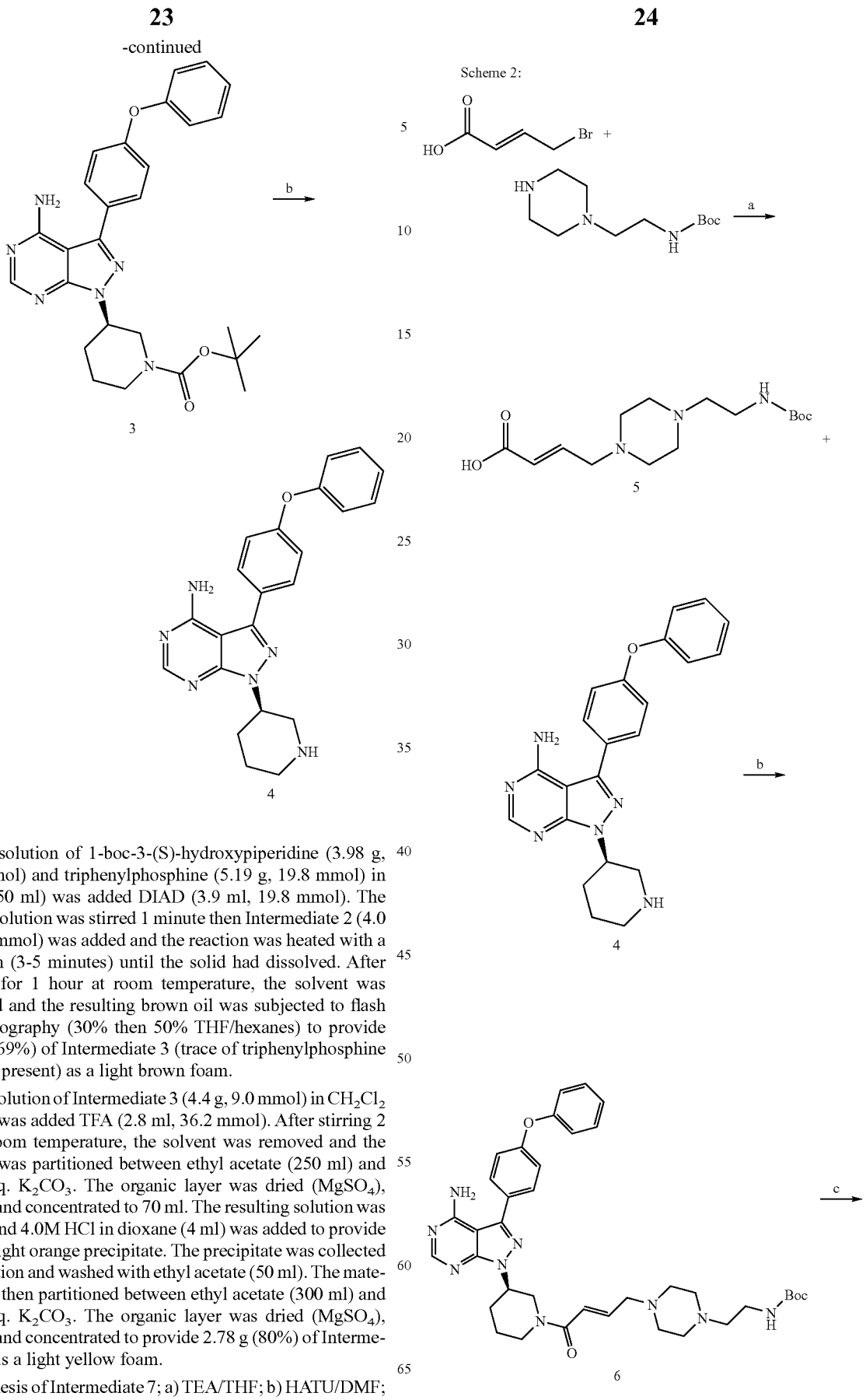

To a solution of 1-boc-3-(S)-hydroxypiperidine (3.98 g, 19.8 mmol) and triphenylphosphine (5.19 g, 19.8 mmol) in THF (150 ml) was added DIAD (3.9 ml, 19.8 mmol). The yellow solution was stirred 1 minute then Intermediate 2 (4.0 g, 13.2 mmol) was added and the reaction was heated with a heat gun (3-5 minutes) until the solid had dissolved. After stirring for 1 hour at room temperature, the solvent was removed and the resulting brown oil was subjected to flash chromatography (30% then 50% THF/hexanes) to provide 4.45 g (69%) of Intermediate 3 (trace of triphenylphosphine oxide is present) as a light brown foam.

To a solution of Intermediate 3 (4.4 g, 9.0 mmol) in CH$_2$Cl$_2$ (20 ml) was added TFA (2.8 ml, 36.2 mmol). After stirring 2 hrs at room temperature, the solvent was removed and the residue was partitioned between ethyl acetate (250 ml) and dilute aq. K$_2$CO$_3$. The organic layer was dried (MgSO$_4$), filtered and concentrated to 70 ml. The resulting solution was stirred and 4.0M HCl in dioxane (4 ml) was added to provide a thick light orange precipitate. The precipitate was collected by filtration and washed with ethyl acetate (50 ml). The material was then partitioned between ethyl acetate (300 ml) and dilute aq. K$_2$CO$_3$. The organic layer was dried (MgSO$_4$), filtered and concentrated to provide 2.78 g (80%) of Intermediate 4 as a light yellow foam.

Synthesis of Intermediate 7; a) TEA/THF; b) HATU/DMF; c) 4.0M HCl/Dioxane.

To a solution of 4-bromocrotonic acid (72 mg, 0.44 mmoles) in THF (3 mL) was added a solution of TEA (0.18 mL, 1.3 mmoles) and 1-(2-N-Boc-aminoethyl)piperazine (0.1 g, 0.44 mmoles) in THF (1 mL). After stirring the solution for 2 hr at room temperature the solvent was removed to provide crude Intermediate 5 which was used without further purification.

To a solution of Intermediate 4 (0.1 g, 0.26 mmoles) and Intermediate 5 in DMF (2 mL) was added HATU (98 mg, 0.26 mmoles). The reaction solution was stirred 30 min at room temperature then diluted with EtOAc (50 mL) and washed with dilute aq. NaHCO$_3$ (2×50 mL). The organic layer was dried (MgSO$_4$), filtered and then concentrated. The resulting residue was purified by flash chromatography (10% MeOH/CH$_2$Cl$_2$) to provide 0.12 g (68%) of Intermediate 6.

Intermediate 6 (0.12 g, 0.18 mmoles) was stirred for 10 min in 4.0 M HCl/Dioxane (1 mL). The solution was concentrated and then stirred in EtOAc to form a precipitate which was collected by filtration and dried under vacuum to provide 0.16 g of Intermediate 7 as a light yellow solid. EM (calc.): 581.32; MS (ESI) m/e (M+1H)+: 582.25.

Synthesis of Compound 3—Btk Activity Probe; a) HATU/TEA, DMF.

Scheme 3:

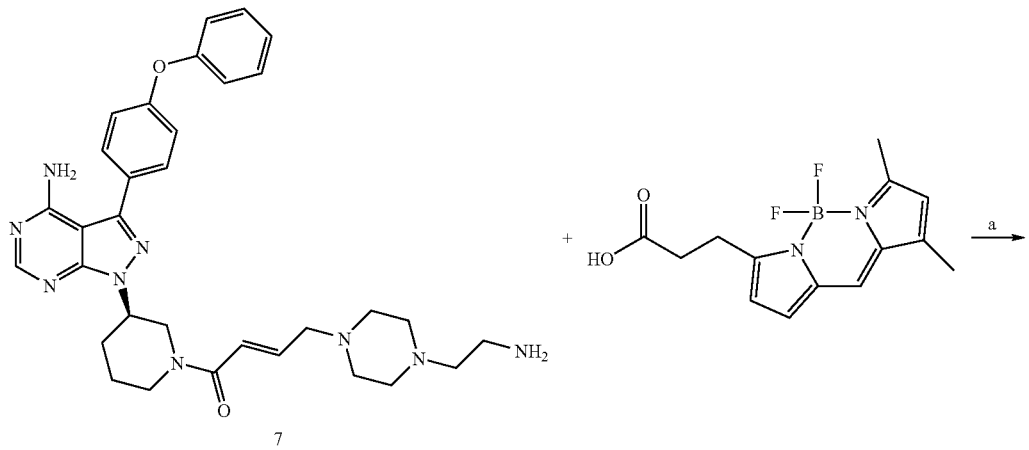

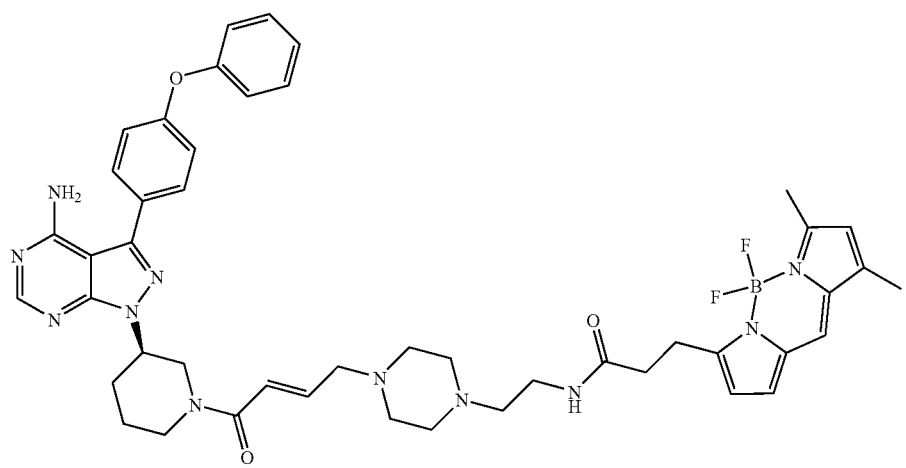

Compound 3

To a solution of Intermediate 7 (40 mg, 69 μmoles) and 4,4-difluoro-5,7-dimethyl-4-bora-3a,4a-diaza-s-indacene-3-propionic acid (10 mg, 34 μmoles) in DMF (1 mL) was added TEA (40 μml) and HATU (14 mg, 38 μmoles). The solution was stirred 1.5 hr at room temperature and then diluted with EtOAc (50 ml) and washed with dilute aq. NaHCO$_3$ (2×50 mL). The aqueous layers were combined and reextracted with EtOAc (20 mL). The organic layers were combined, dried (MgSO$_4$), filtered and then concentrated. The resulting orange/brown residue was purified by flash chromatography (20% MeOH/CH$_2$Cl$_2$) to provide 25 mg (85%) of Compound 3 as an orange/brown solid. EM (calc.): 855.43; MS (ESI) m/e (M+1H)+: 856.25.

Synthesis of Compound 4

Synthesis of Compound 4: a) TEA/THF

Methods for Testing and Using Btk Activity Probes

In some embodiments, the ability of a test Btk activity probe to label Btk was tested by incubating increasing concentrations of the probe with an amount of purified enzyme. Following this step, bodipy-labeled protein is visualized following SDS-PAGE by scanning the gel with a densitometer or fluorescent scanner. In the case of the illustrative Btk activity probe, Compound 3, the intensity of the labeled protein band increased in direct proportion to the concentration of probe added and reached saturation at 1 μM, indicating that the probe quantitatively labeled Btk (FIG. 2b).

Figure 2C:
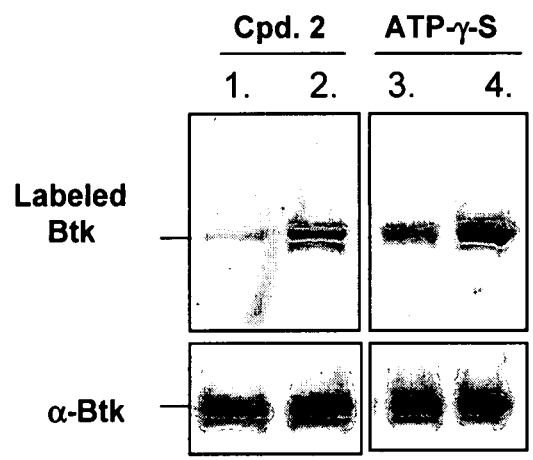

Further, probe labeling was substantially reduced if Btk is pre-incubated with either ATP-γ-S or Compound 2 (FIG. 2c), indicating that the Btk activity probe, like its parent Compound 2, irreversibly modified Btk in the ATP binding pocket.

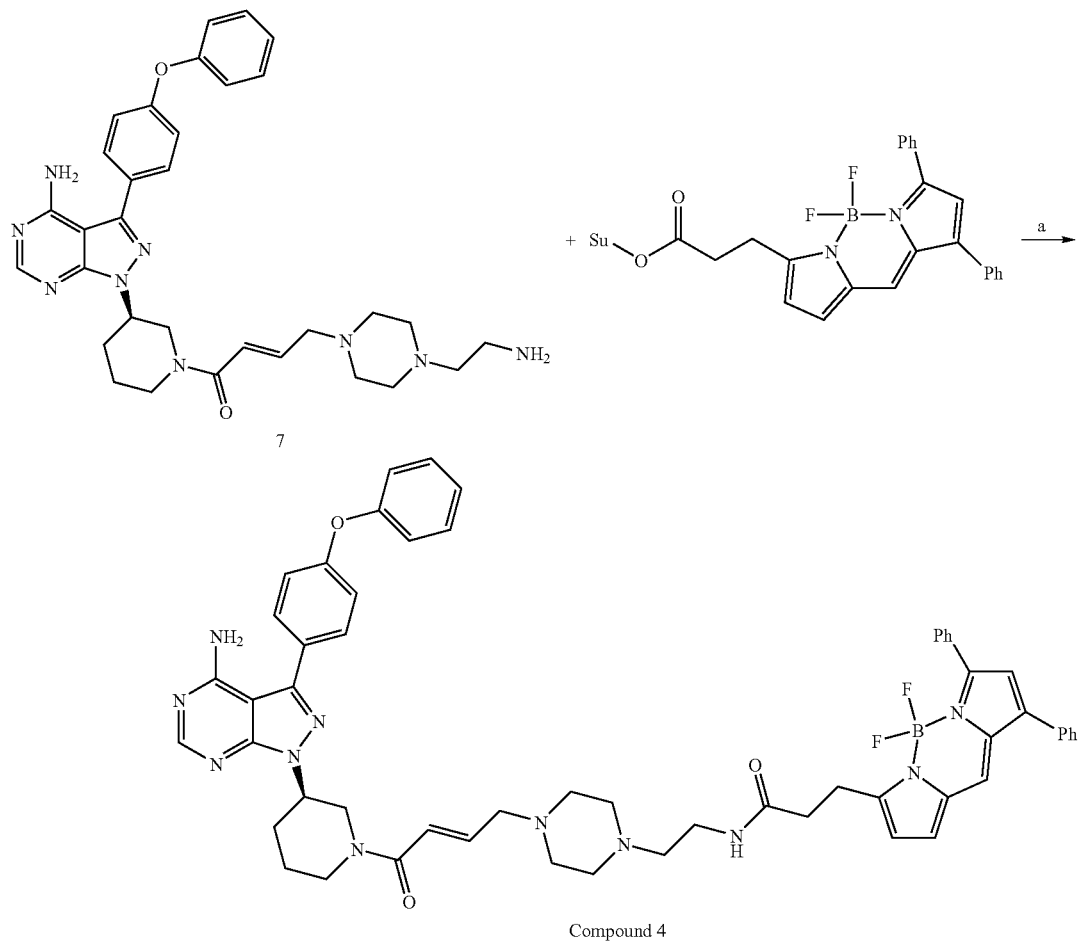

Scheme 4:

Compound 4

To a solution of Intermediate 7 (11 mg, 20 μmoles) and TEA (0.5 mL) in THF (3 mL) was added 4,4-difluoro-5,7-diphenyl-4-bora-3a,4a-diaza-s-indacene-3-propionic acid succinimidyl ester (5 mg, 9.7 μmoles). After stirring for 4.5 hr at room temperature, the reaction solution was diluted with EtOAc (50 mL) and washed with dilute aq. NaHCO$_3$ (1×50 mL). The organic layer was dried (MgSO$_4$), filtered and then concentrated. The resulting bright red residue was purified by flash chromatography (20% MeOH/CH$_2$Cl$_2$) to provide 7.7 mg (81%) of Compound 4 as a red foamy solid. EM (calc.): 979.46; MS (ESI) m/e (M+1H)+: 980.32.

Activation of Btk by phosphorylation at tyrosine 551 is inferred from structural studies to occur via a conformational change that renders the ATP binding pocket accessible to substrate.

Figure 2D:
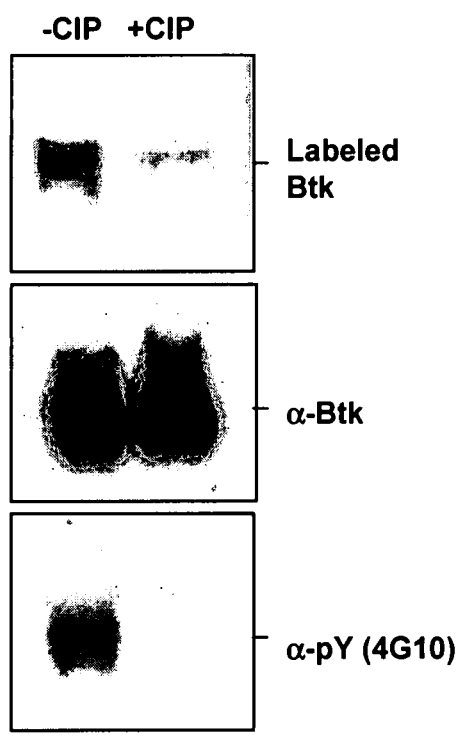

In other embodiments, the determination of whether a test Btk activity probe only accesses and labels the ATP binding pocket when Btk is in its phosphorylated conformation and not in its non-phosphorylated conformation was made by comparing the probe labeled active, phosphorylated Btk to Btk that had been dephosphorylated in vitro by phosphatase treatment. If phosphatase treatment greatly diminished the intensity of labeling (see, e.g., FIG. 2d for illustrative Btk activity probe, Compound 3), then the probe preferentially labels the phosphorylated form of Btk. Without limiting the scope of the methods described herein, in some embodiments, the residual labeling seen in the phosphatase-treated Btk lane in FIG. 2 represents incomplete dephosphorylation, although little or no residual tyrosine phosphorylation was detectable with the sequence-independent, anti-phosphotyrosine 4G10 antibody. In some embodiments, partial denaturation of the kinase domain during phosphatase treatment allowed probe access to the ATP pocket in a small fraction of the enzyme population.

Figure 3A:
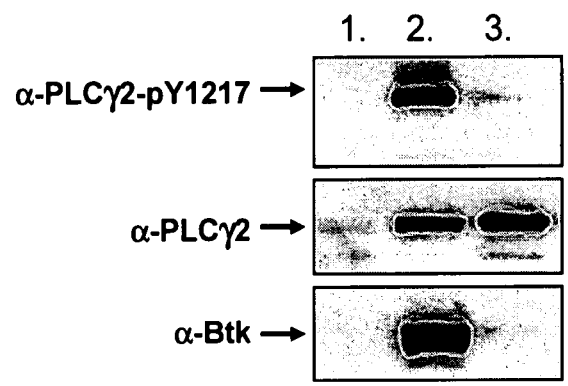
FIG. 3 presents an illustrative expression analysis and probe labeling of recombinant Btk in transfected mammalian cells. (a) Western blot analysis of lysates from non-transfected 293H cells (lane 1), cells transiently co-transfected with expression plasmids for His6-Btk (6×His tag disclosed as SEQ ID NO: 2) and PLCγ2-V5 (lane 2), or cells transfected with PLCγ2 alone (lane 3). The gel was blotted with an anti-phosphotyrosine-1217-PLCγ2 antibody (upper panel), stripped and re-blotted sequentially with anti-PLCγ2 (middle panel) and anti-Btk antibodies (bottom panel). (b) Non-transfected 293H cells (lane 1) or cells transiently transfected with His6-Btk (6×His tag disclosed as SEQ ID NO: 2) were labeled with an illustrative Btk probe (Compound 3) and then lysed and treated with Ni-NTA beads to precipitate His-Btk (lanes 1, 2) or lysed and treated with Ni-NTA beads followed by probe labeling (lane 3). The lower panel shows an anti-Btk western of the same gel. (c) 293H cells stably co-expressing His-Btk and PLCγ2 treated with increasing concentrations of the illustrative probe (left to right: 0, 0.007, 0.024, 0.08, 0.27, 0.9, 3, 10 µM) added to the culture medium (top panel). The gel was then sequentially blotted with anti-phosphotyrosine-1217-PLCγ2 (middle panel) or anti-Btk antibodies (bottom panel). (d) Non-transfected 293H cells (lane 5) or cells transiently co-transfected with PLCγ2 and wild type (lane 1) or K430A (lane 2), C481A (lane 3), Y551A (lane 4) mutants of Btk labeled with the illustrative probe. Following scanning for probe labeling, the gel was sequentially blotted with anti-Btk (right, upper panel), anti-phosphotyrosine-1217-PLCγ2 (right, middle panel), and anti-PLCγ2 antibodies (right, lower panel).
Figure 3B:
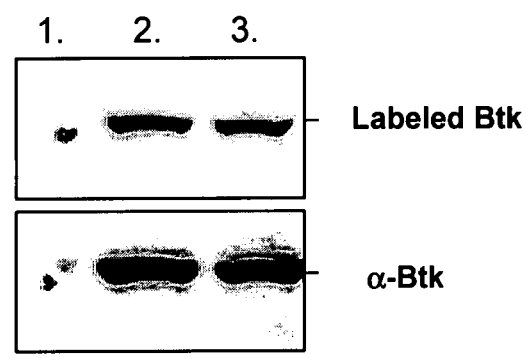
Figure 3C:
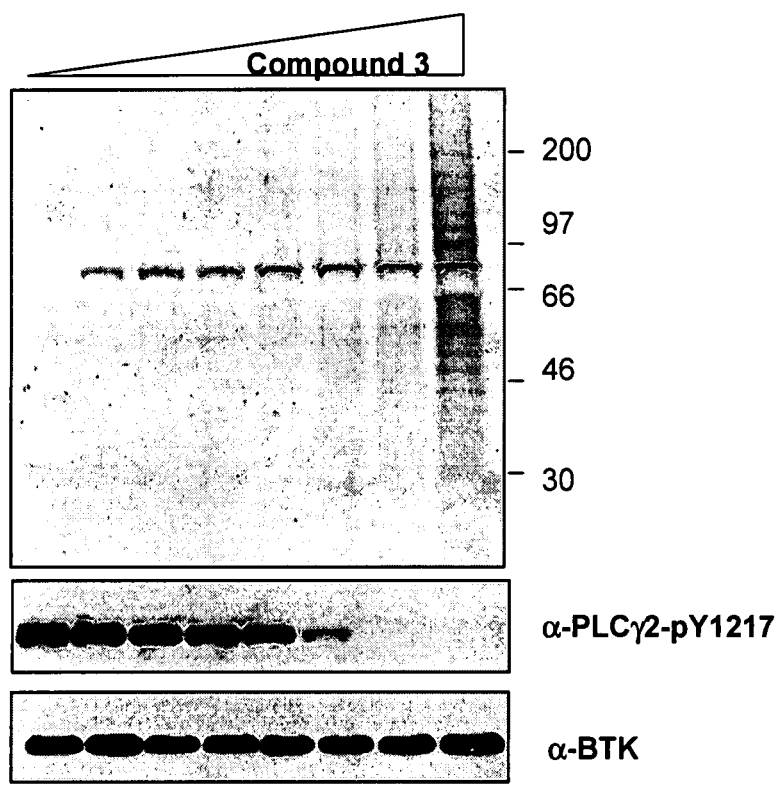

To address the cell permeability and labeling specificity in intact cells for a test Btk activity probe, mammalian 293H cells transiently or stably expressing epitope-tagged forms of Btk and/or PLCγ2, an endogenous substrate for Btk in B cells was used. For example, in this system, phosphorylation of PLCγ2 at tyrosine 1217 demonstrates the activity of ectopically expressed Btk (FIG. 3a). In pull down experiments using Ni-NTA coated beads to purify His-tagged Btk, the His-tagged Btk expressed transiently in 293H cells was efficiently labeled when lysates were incubated with an illustrative probe (Compound 3), either before (FIG. 3b, lane 2) or after Ni-NTA pull down (FIG. 3b, lane 3). No labeling was observed in untransfected cells, confirming that probe labels Btk. In 293H cells stably co-expressing Btk and PLCγ2 treated with increasing concentrations of probe, dose-dependent labeling of a single major protein band of the molecular weight expected for BTK was observed, with little non-specific labeling of other proteins (FIG. 3c). A corresponding dose dependent inhibition of PLCγ2 phosphorylation at Tyr 1217 indicates that irreversible binding of the probe suppresses the constitutive kinase activity of Btk. The $EC_{50}$ for labeling of Btk is estimated to be ~0.2 μM, in good agreement with a corresponding $IC_{50}$ value of 0.3 μM for probe inhibition of PLCγ2 phosphorylation quantitated independently by an ELISA method. These results indicate that the Btk probe penetrates the cell membrane and can be used to selectively label Btk and inhibit its kinase activity in intact cells.

Figure 3D:
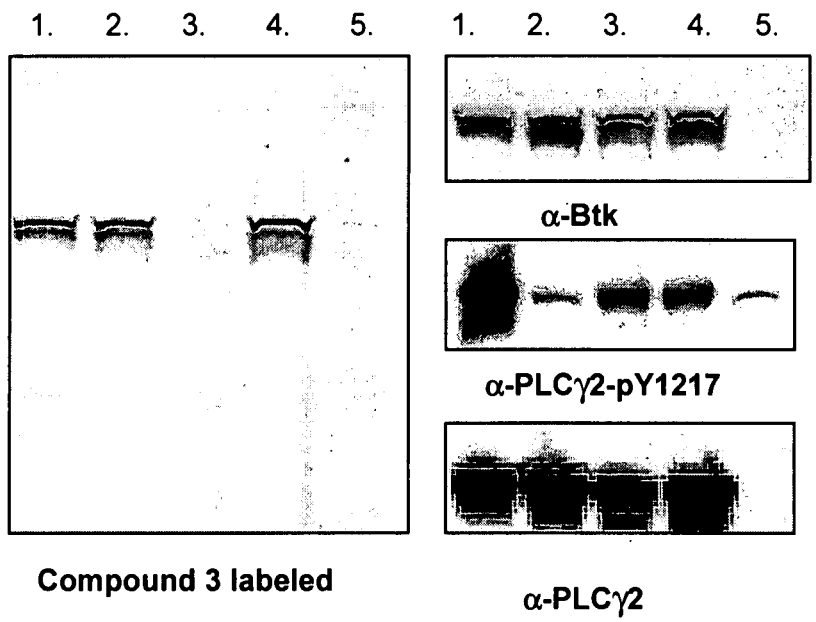

In some embodiments, a transient expression system, coupled with site-directed mutagenesis, is used to assess the enzyme structural requirements for probe labeling in cells and to determine whether a test Btk activity probe modifies Cys 481 in Btk. For example, probe labeling was assessed in 293H cells transiently co-expressing PLCγ2 and wild type or mutant forms of Btk (FIG. 3d). A Cys 481 to Ala mutation abrogated labeling by the illustrative Btk activity probe, Compound 3, but only slightly reduced Btk kinase activity. Mutating the catalytic Lys 430 residue to Ala inactivated the kinase activity but had no effect on probe labeling. The mutant with a Tyr 551 to Ala activation loop change was also labeled, suggesting that this mutation in Btk yields a partially active enzyme.

The probes described herein label Btk at the non-catalytic Cys 481 and that in some embodiments, probe labeling does not require the catalytic machinery per se. As such it differs from canonical activity-based probes that target the enzyme catalytic machinery directly. In some embodiments, Btk undergoes a phosphorylation dependent conformational change that is tightly coupled to ATP binding and kinase activation. In some embodiments, effective labeling by a probe requires Btk to be in its active conformation in order to directly detect Btk activity in cells. In other embodiments, effective labeling by a Btk activity probe does not require Btk to be in its active conformation in order to directly detect Btk activity in cells.

Figure 4A:
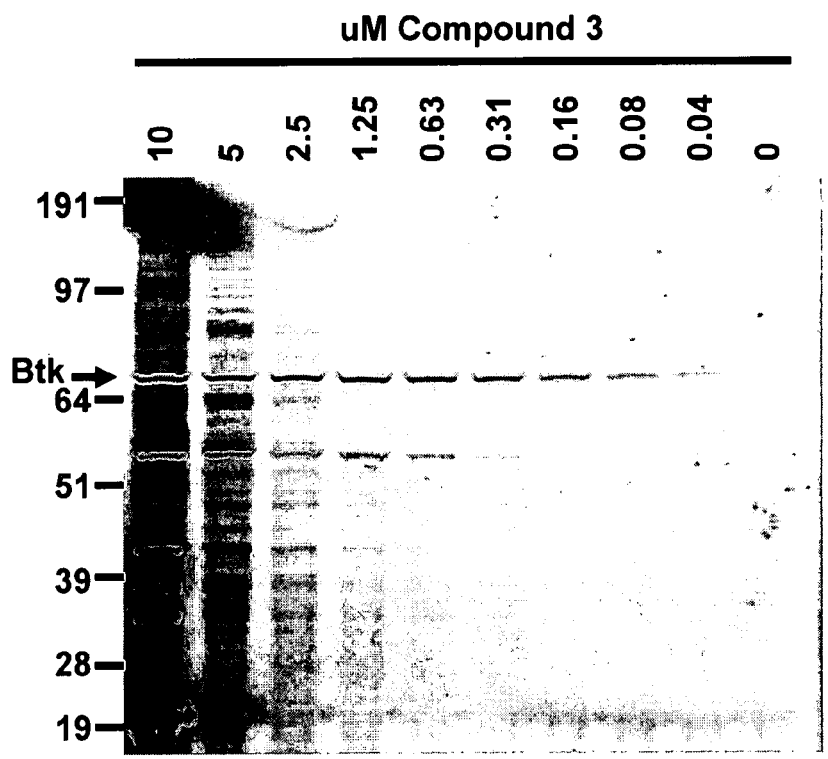
FIG. 4 presents an illustrative probe labeling of endogenous Btk in a B cell lymphoma cell line. (a) DOHH2 B-cells ($4 \times 10^5$ cells/lane) treated with increasing concentrations of the illustrative probe Compound 3 for one hour, lysed, and analyzed by SDS-PAGE. (b) DOHH2 B-cells ($4 \times 10^5$ cells/lane) treated with increasing concentrations of Compound 4 for one hour, lysed, and analyzed by SDS-PAGE. Btk is not significantly labeled by Compound 4, illustrating that not all combinations of Compound 2 with a fluorophore are specific Btk kinase probes. (c) DOHH2 cells ($4 \times 10^5$ cells/lane) pre-incubated with increasing concentrations of the inhibitor Compound 2 for 1 hour followed by incubation with 2 µM Compound 3 for one hour. (d) Densitometry of the Btk band intensity from gel in 4(c) illustrating linear relationship between inhibitor concentration and band intensity.
Figure 4B:
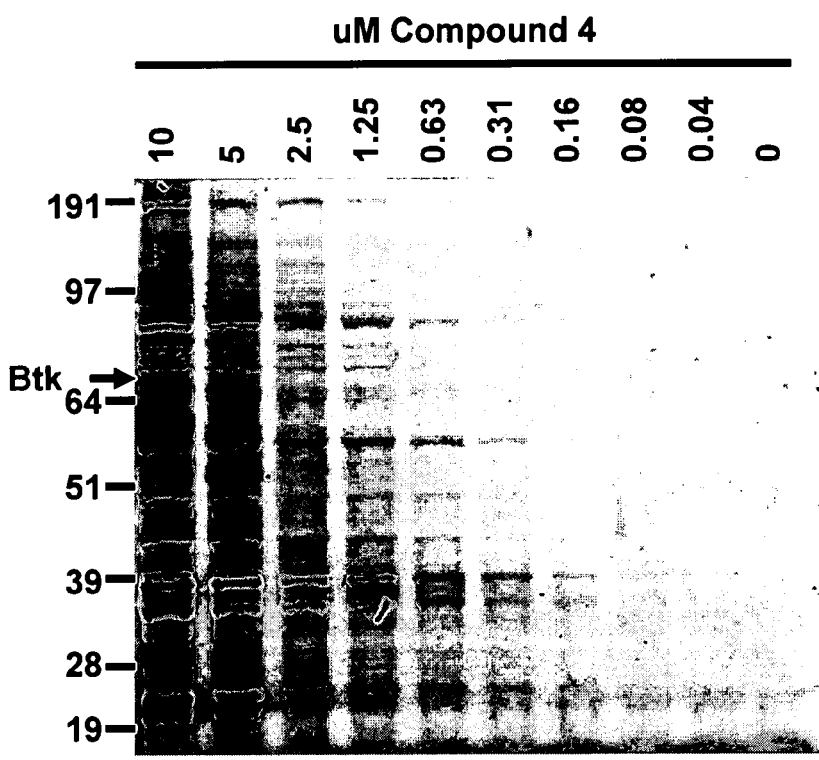

In some embodiments, to determine if a test Btk probe detects endogenous levels of Btk activity, label cultured B cells such as Ramos or DOHH2 B cells were used. For example, dose dependent labeling of Btk (using the illustrative Btk activity probe, Compound 3) was observed, with an $EC_{50}$ for labeling of ~0.2 μM, in good agreement with an $IC_{50}$ of 0.23 μM determined for the probe in a functional assay that quantitated intracellular calcium mobilization in Ramos cells following B cell receptor activation (Table 1; FIG. 4a). In contrast, the probe Compound 4 is not a strong Btk activity probe because it does not significantly label a band corresponding to Btk in DOHH2 cells (FIG. 4b).

Figure 4C:
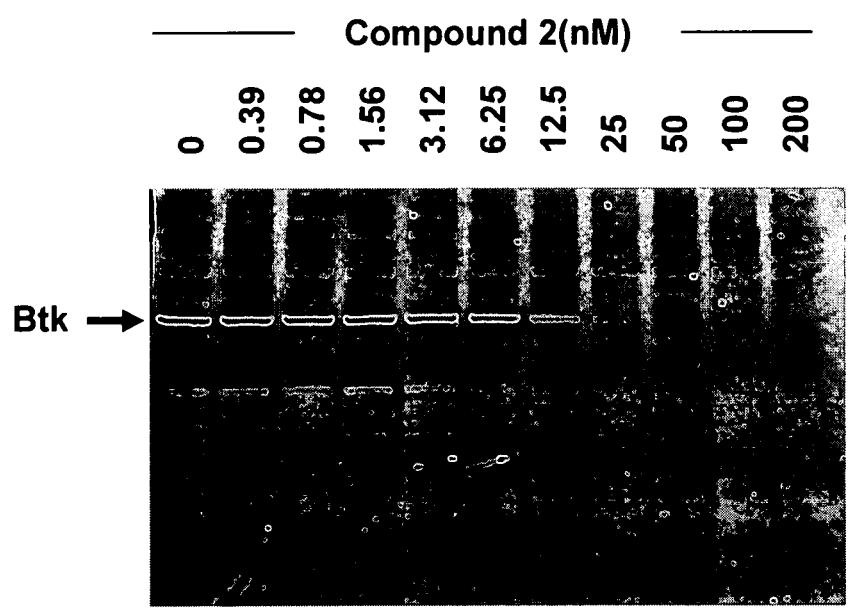
Figure 4D:
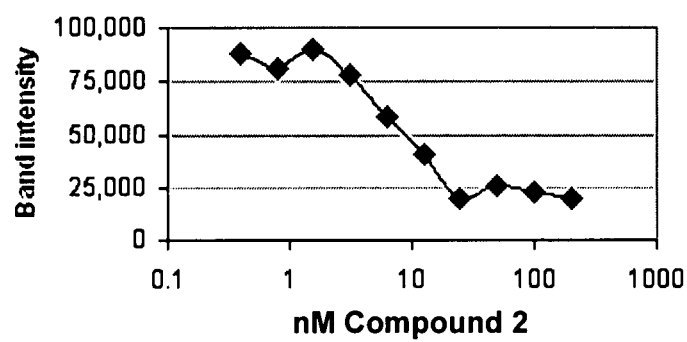
Figure 5A:
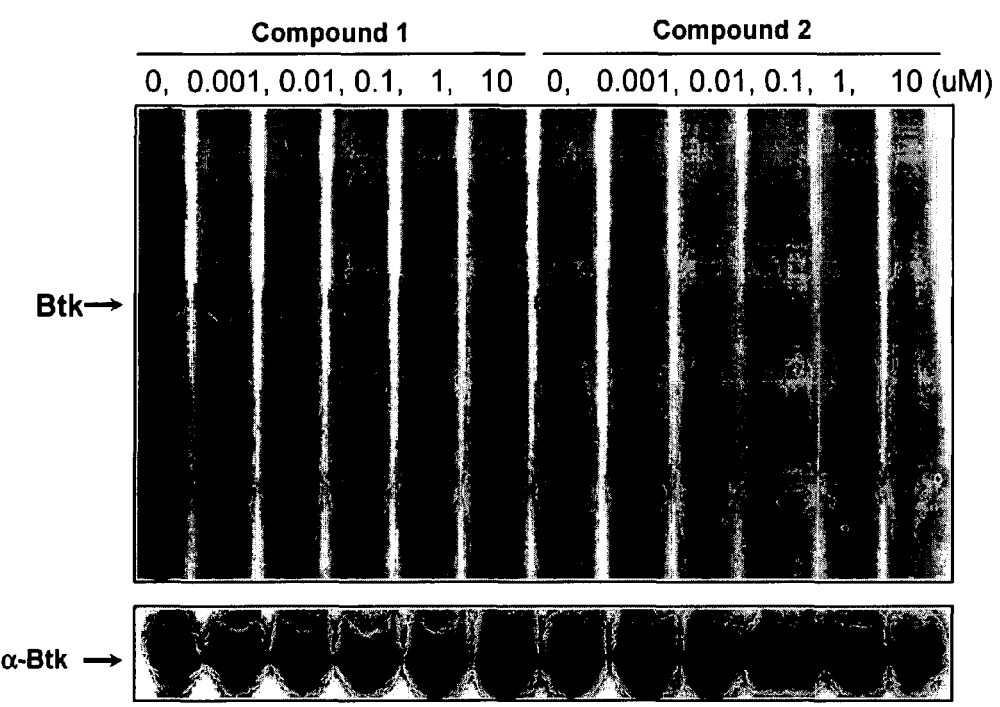
FIG. 5 presents an illustrative probe labeling of splenic B-cells ex vivo to show use of the probe to measure inhibition of Btk, the duration of inhibition of Btk in vivo, and the specificity of the probe for Btk. (a) Freshly prepared splenocytes pre-incubated with increasing concentrations of either Compound 1 or Compound 2 followed by labeling with 1 µM Compound 3. Cells were lysed, fractionated by SDS PAGE, and fluorescently scanned. (b) Time course of ex vivo probe labeling of splenocytes from mice dosed orally with 30 mg/kg compound 2. Representative data obtained with splenocytes from one of two independently treated mice are shown. (c) Splenocytes isolated 16 h after oral dosing of saline (Sa.), formulation buffer (veh.), or Compound 2 (30 mg/kg at t=0 and 2 h) from Xid (left panel) or wild-type CBA (right panel) mice and labeled with probe (Compound 3) ex vivo The lower panels in (a), (b), and (c) show anti-Btk immuno-blot of the same gels.

In some embodiments, a competition experiment is used to test the suitability of a test Btk activity probe for assessing inhibitor $IC_{50}$s in B cells. For example, probe labeling with the illustrative Btk activity probe, Compound 3, was blocked by pre-incubation with Compound 2 in a dose dependent manner, yielding an $IC_{50}$ value for Compound 2 (~10 nM) similar to that obtained with the calcium mobilization assay (Table 1: FIG. 4c). As described herein, similar competition assays have also been successfully carried out using reversible Btk inhibitors (FIG. 5a). Thus, in other embodiments, probe competition studies are used as an alternative means of quantitating Btk inhibitor potencies in cellular assays.

Methods for Using Btk Activity Probes in Assessing Pharmacodynamic Behavior

To explore the utility of a test Btk activity probe in assessing compound pharmacodynamics (PD) in preclinical pharmacology models, labeled mouse Btk enzyme ex vivo in splenocytes isolated from Balb/c mice using the test probe were employed. Because mouse and human Btk share sufficient sequence identity at the amino acid level, cross reactivity of a test probe with the mouse enzyme should be present. For example, in one embodiment, for the illustrative Btk activity probe, Compound 3, a visible band of the appropriate MW was detected when mouse splenocytes were activated with anti-IgM prior to labeling. Although a higher level of background labeling was evident in splenocytes compared to the transfected 293H cells, labeling of only the 70 kD band was effectively competed away by irreversible (Compound 2) and reversible (Compound 1) Btk inhibitors, suggesting that this band was indeed mouse Btk (FIG. 5a). The labeling of Btk is further confirmed by detection of Btk at 70 kD by western blot (FIG. 5a).

Figure 5B:
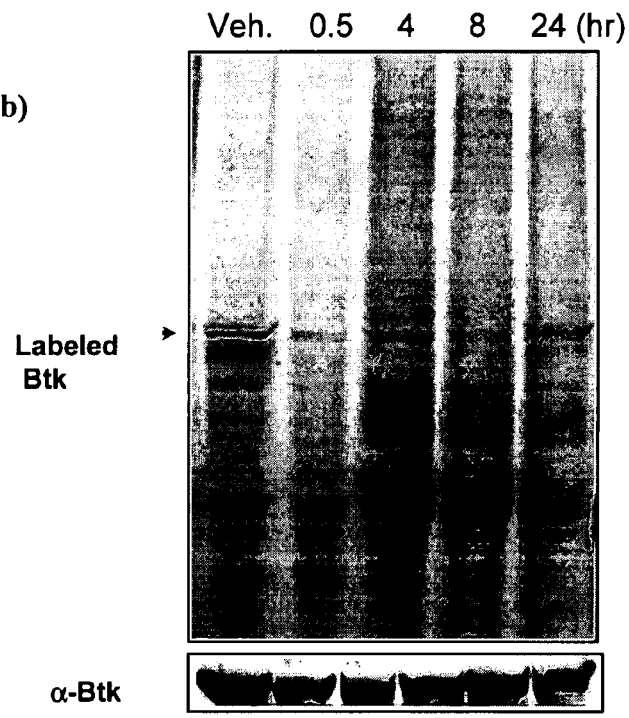
Figure 5C:
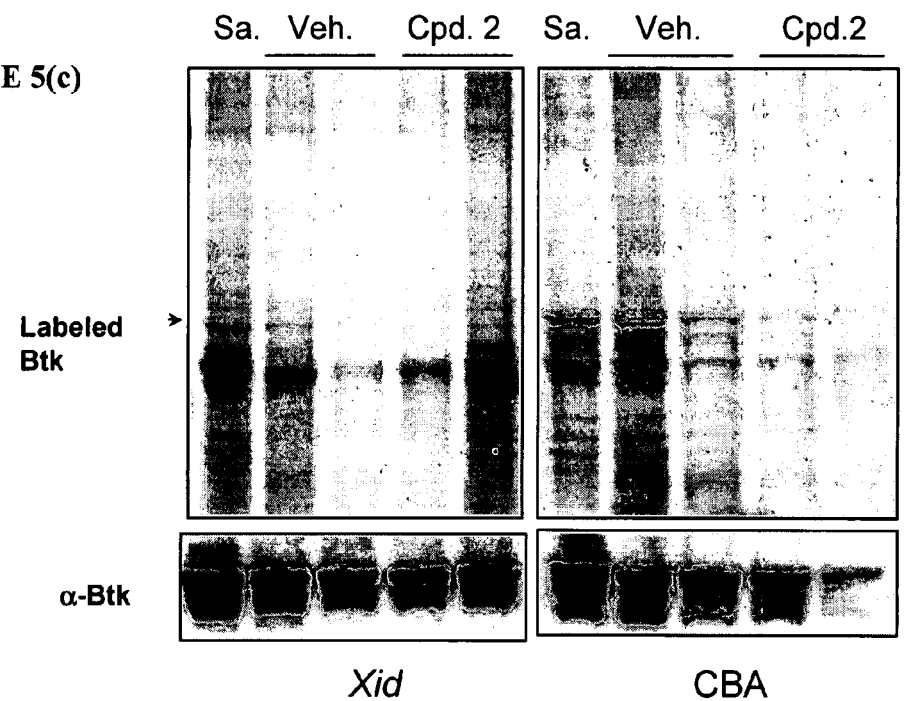
Figure 6A:
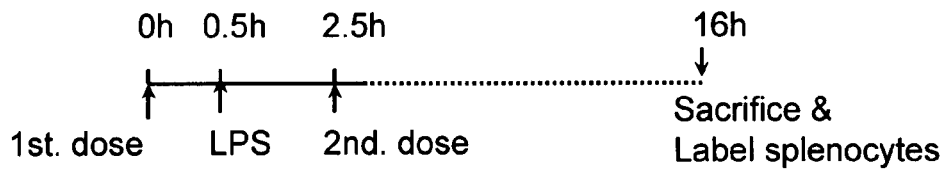
FIG. 6 presents an illustrative example of ex vivo labeling of splenocytic Btk in inhibitor-dosed mice. Panel (a) shows the treatment protocol. Mice were orally dosed with Btk inhibitors (Compound 1 or Compound 2 at 0 hour), challenged with 20 µg lipopolysaccharide (LPS) 0.5 hour post-dose, dosed again at 2.5 hour with a second oral dose of Compound 1 or Compound 2 and the mice were sacrificed at 16 hour. Splenocytes were then harvested and labeled for 1 h with 1 µM Compound 3, lysed, fractionated by SDS PAGE and quantitated by fluorescent scanning. Panel (b) shows results of probe labeling of splenocytic Btk from Compound 1 (the reversible inhibitor) orally dosed at various dosages. Panel (c) shows labeling of Compound 2 (the irreversible inhibitor) dosed mice at various dosages. (Sa.=dosed with saline only, or vehicle=formulation buffer). The probe labeled Btk protein bands and anti-Btk immuno-reactive bands are indicated. The asterisk (*) in (c) denotes labeling of BSA protein that was originally included in the labeling buffer and was later omitted in the subsequent experiments. The lower panels in (b) and (c) show anti-Btk immunoblot of the same gels. The total Btk as determined from the intensity of anti-Btk immuno-reactive protein band was used to normalize the amount of probe labeling in each lane. The bar graphs in (b) and (c) show averaged inhibition of labeling from at least two independently dosed mice for each condition. (% activity=normalized pixel values of compound treated samples/pixel values of vehicle treated samples).
Figure 6B:
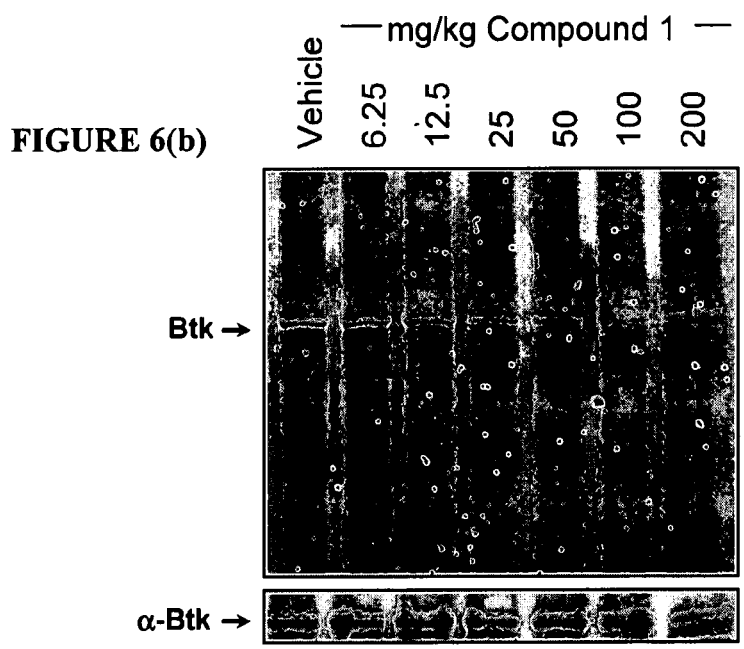
Figure 6B:
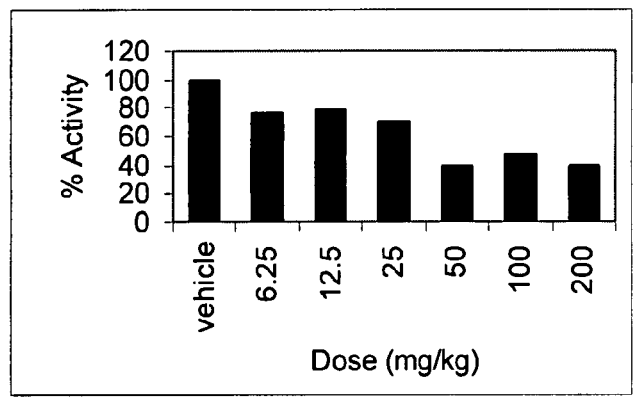
Figure 6C:
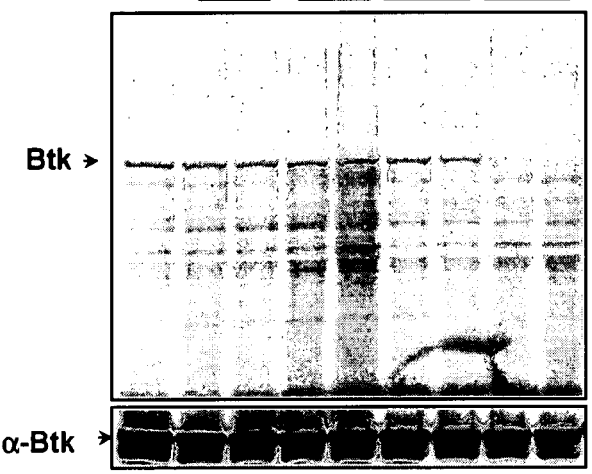
Figure 6C:
Figure 6C:
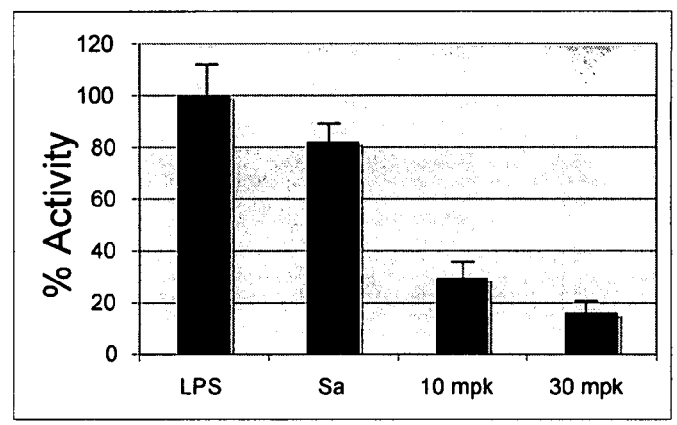

In one illustrative PD study, splenocytes collected from naïve mice at different time points after oral dosing with an irreversible Btk inhibitor were subsequently incubated with a test probe to determine detection of target modulation in vivo via ex vivo labeling. With the illustrative Btk activity probe, Compound 3, competition for probe labeling was observed and splenic B cell Btk activity was suppressed by the irreversible inhibitor for at least 14 hours post dosing, with activity reappearing at the 24 hour time point (FIGS. 5b and 5c). The total Btk protein levels remained relatively constant throughout the time course as shown by anti-Btk immunoblotting, suggesting that Compound 2 inhibited Btk activity rather than depleting the cellular Btk protein level. In some embodiments, the reappearance of Btk activity represents turnover of Btk in splenocytes following clearance of the inhibitor from the circulation.

To further confirm that labeling by the test probe ex vivo reflects BCR signaling activity, the labeling profile in splenocytes from xid mice were compared with their isogenic, wild type CBA parent strain. For example, Xid mice are phenotypically null for Btk activity due to an Arg 28 to Cys mutation in the Btk PH domain that impairs phosphatidylinositol-3,4,5-triphosphate (PIP3) binding capability. The mutant enzyme is defective in membrane localization, remains in the cytoplasm in an inactive conformation, and consequently fails to transduce signals upon BCR activation. With the illustrative Btk activity probe, significant labeling of Btk is observed in splenocytes from CBA mice that was blocked by prior oral administration of Compound 2 whereas little or no labeling was seen in samples from xid mice (FIG. 5c). In one embodiment, the Btk activity probe discriminates against inactive Btk from xid mice, consistent with the conformational selectivity of this reagent, and confirming that probe labeling reflects functional Btk activity in BCR signal transduction in vivo.

In another aspect, the Btk activity probes described herein are used to characterize and measure the pharmacodynamics of compounds that interact with Btk, not only in animal disease models, but also in human patients or other mammalian subjects. By way of example only, in some embodiments, Compound 3 assesses pharmacodynamics in a mouse model for inflammation. Dose response experiments were conducted in LPS-challenged mice with the irreversible and reversible Btk inhibitors and quantitated the results of ex vivo labeling by densitometry. Dose dependent inhibition of probe labeling was observed for both compounds, although inhibition with the less potent, reversible inhibitor was seen only at substantially higher doses and was less complete (FIG. 6). Similar results were seen in the absence of LPS-challenge and the comparative dose responses for probe labeling are consistent with the dose responses seen in both efficacy and biomarker modulation studies of the two compounds in a mouse collagen-induced arthritis model.

EXAMPLES

Reagents

Biochemical reagents, tissue culture media, antibiotics, and antibodies used in this study were purchased from commercial sources and used according to the manufacturer's instructions. Cell lines 293H (11631-017, Invitrogen), DOHH2 (ACC 47, DSMZ) and Ramos RA 1 (CRL-1596, ATCC) were routinely cultured in D-MEM and RPMI, respectively, supplemented with 10% FBS and non-essential amino acids (Invitrogen). Antibiotics blasticidin and G418 (Invitrogen) were included in the culture medium when necessary to select or to maintain transfected cells. Recombinant, active Btk and Ni-NTA sepharose beads were purchased from Upstate Biochem, and from Qiagen, respectively. CIP (calf intestinal alkaline phosphatase) was obtained from NEB (New England Biolabs). Antibodies to Btk (monoclonal mouse anti-human Btk from BD transduction laboratories), PLCγ2, phosphotyrosine 1217-PLCγ2, phosphotyrosine 4G10 (Cell Signaling), and anti-human IgM (from Jackson laboratory) were diluted and used in western blot detection as recommended by the manufacturers.

Example 1

Kinase Assays

Kinase activity for Btk, Abl, c-met, ITK, LCK, and EGFR was determined using a time-resolved fluorescence resonance energy transfer (TR-FRET) methodology. Measurements were performed in a reaction volume of 50 μl using 96-well assay plates. Kinase enzyme, inhibitor, ATP (at the Km for the kinase), and 1 μM peptide substrate (Biotin-AVLESEEELYSSARQ-NH2) (SEQ ID NO: 1) were incubated in a reaction buffer composed of 20 mM Tris, 50 mM NaCl, MgCl$_2$ (5-25 mM depending on the kinase), MnCl$_2$ (0-10 mM), 1 mM DTT, 0.1 mM EDTA, 0.01% bovine serum albumin, 0.005% Tween-20, and 10% DMSO at pH 7.4 for one hour. The reaction was quenched by the addition of 1.2 equivalents of EDTA (relative to divalent cation) in 25 μL of 1× Lance buffer (Perkin-Elmer). Streptavidin-APC (Perkin-Elmer) and Eu-labeled p-Tyr100 antibody (Perkin-Elmer) in 1× Lance buffer were added in a 25 μL volume to give final concentrations of 100 nM and 2.5 nM, respectively, and the mixture was allowed to incubate for one hour. The TR-FRET signal was measured on a multimode plate reader with an excitation wavelength of 330 nm and detection wavelengths of 615 and 665 nm. Activity was determined by the ratio of the fluorescence at 665 nm to that at 615 nm. For each compound, enzyme activity was measured at various concentrations of compound. Negative control reactions were performed in the absence of inhibitor in replicates of six, and two no-enzyme controls were used to determine baseline fluorescence levels. Inhibition constants {Ki(app)} were obtained using the program BatchKi (23). IC$_{50}$s were obtained according to this equation: IC$_{50}$={Ki(app)/(1+[ATP]/KmATP)}+[E]$_{total}$/2; for all kinases, [ATP]=KmATP, [Btk]$_{total}$=0.5 nM and [Lck]$_{total}$=6 nM.

Example 2

Btk Labeling In Vitro

To label Btk in vitro, Compound 3 was diluted from a 10 μM DMSO stock to indicated concentrations (FIG. 2) and incubated with 1 μg (0.13 μM) of purified, active Btk in 100 μl reaction buffer (20 mM Tris-HCl, pH 7.2, 150 mM NaCl) for 1 hour at 37° C. The reactions were stopped and labeling quenched by boiling in 1×SDS sampling buffer (2% SDS, 62.5 mM Tris-HCl pH 6.8, 5% 2-mercaptoethanol) at 90° C. for 10 min. The reaction mixes were then fractionated by electrophoresis on a gradient (4-20%) SDS-polyacrylamide gel (Invitrogen) to separate unincorporated Compound 3 from labeled Btk. The gel was scanned using a Molecular Dynamics Typhoon scanner (Ex=532 nm and Em=580 nm) to detect the labeled Btk protein bands and quantitated using ImageQuant software. Dephosphorylation of Btk was carried out by incubating 1 μg of purified Btk (Upstate biochem) with 10 units of CIP (NEB) in a 10 μl reaction mix at 37° C. for 1 hour and the reaction was stopped by addition of 10 mM sodium orthovanadate. Dephosphorylated Btk was used in subsequent labeling experiments without further purification.

Example 3

Btk Labeling in Cell Lysates and Intact Mammalian Cells

Transient transfection of 293H cells was carried out using Qiagen column purified plasmid DNA and transfectamine 2000 (Invitrogen) according to the manufacturer's descriptions. Probe labeling experiments were performed 24 hours post transfection either by incubation of transfected cells in reduced serum medium (Opti-MEM 1, Invitrogen) containing diluted Compound 3 (0.1 μM) or by addition of appropriately diluted Compound 3 to cell lysates for 1 hour at 37° C. A stable cell line co-expressing Btk and PLCγ2 was generated by co-transfection of pDES plasmids (Invitrogen) encoding His6-Btk (6×His tag disclosed as SEQ ID NO: 2) and PLCμ2-V5, followed by clonal selection of G418/blastocidin doubly resistant colonies. The candidate clones were further characterized by immunoblotting to confirm that the transfected Btk was active and phosphorylated at the activation (Y551) and auto-phosphorylation (Y223) sites (data not shown). The selected co-expressor cell line was routinely maintained in D-MEM containing 10% FBS, 1× non-essential amino acids, 1× antibiotics, and supplemented with 200 µg/ml G418 and 25 µg/ml blastocidin. To label transfected 29311 cells, ~5×10$^5$ cells were incubated in conditioned medium containing 1 µM compound 3 (by direct dilution into medium from a 10 µM DMSO stock) at 37° C. for 1 hour. Cells were then harvested and lysed by incubation in 50 µl of cell lysis buffer (CelLytic M, Sigma) supplemented with 1× protease inhibitor and 1× phosphatase inhibitor cocktails (Calbiochem) for 10 min on ice. The protein concentrations in cell lysates were determined by Bradford protein assay (Pierce). Lysates equivalent to 20 µg of total protein were fractionated on 4 to 20% SDS-gradient gels (Invitrogen), and scanned using a Typhoon densitometer as described above. Labeling of Ramos cells was carried out in identical fashion except RPMI medium was used.

Example 4

Calcium Flux Assay

Calcium flux assay was performed according to the protocol described by the manufacturer (Molecular Devices). Briefly, actively growing Ramos B-cells in RPMI medium supplemented with 10% FBS were washed and re-plated in low serum medium to approximately 5×10$^5$ cells per 100 µl per well in 96-well plate. Compounds to be assayed were dissolved in DMSO, diluted to appropriate concentrations in low serum medium (from 0 to 10 µM final concentrations at a stepwise dilution factor of 0.3), added to each well (the final DMSO concentration was 0.01% in each well) and incubated at 37° in a 5% $CO_2$ incubator for 1 hour. 100 µl calcium assay dye (Calcium 3 assay kit, Molecular Devices) was then added to each well and the incubation was continued for one hour. Compound-treated cells were stimulated with a goat anti-human IgM antibody (80 µg/ml) and the calcium mobilization signal was read in a Flexstation II 384 (Molecular Devices) at excitation and emission wavelengths of 485 nm and 538 nm, respectively, for 200 seconds. The relative fluorescence units (RFU) and the fifty percent inhibition values ($IC_{50}$%) were recorded and analyzed using the SoftMax program (Molecular Devices).

Example 5

Btk Labeling in Mouse Splenocytes Ex Vivo

All animal studies were conducted under protocols approved by the Celera institutional animal care and use committee. Female Balb/c mice were administered by the oral route of the indicated amounts (mg/kg) Btk inhibitors formulated in 0.5% CMC/0.2% Tween 80/water or formulation buffer without inhibitor (vehicle treated mice). LPS was injected intraperitoneally at 20 µg/mouse 30 minutes post compound dosing. Mice were boosted again with the same amounts of inhibitor two hours after LPS injection. In this treatment regimen, vehicle treated mice refers to mice receiving formulation buffer and LPS injections in the absence of inhibitor. Naïve mice refers to mice receiving saline only. Mice were sacrificed by $CO_2$ asphyxiation 16 hours post first compound dosing and spleens were collected in PBS on ice for splenocyte isolation. The spleens were gently ground between 2 glass microscope slides to release splenocytes and erythrocytes in splenocyte preparations were lysed on ice using RBC lysis buffer (Sigma). Connective tissue and cell debris were removed by filtration through 70 µm Cell Strainers (Falcon). The washed splenocyte preparations, typically containing >90% live B cells, were counted and re-suspended in cold RPMI medium and labeled with probe as described in Example 3.

It is understood that the examples and embodiments described herein are for illustrative purposes only and that various modifications or changes are to be included within the spirit and purview of this application and scope of the appended claims. All publications, patents, and patent applications cited herein are hereby incorporated by reference in their entirety for all purposes.

What is claimed is:

1. A Btk activity probe of Formula (I) comprising:

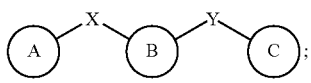

Formula (I)

wherein:
A is an irreversible Btk inhibitor moiety having an alkene group which covalently bonds to a cysteine residue of a Btk enzyme having the structure:

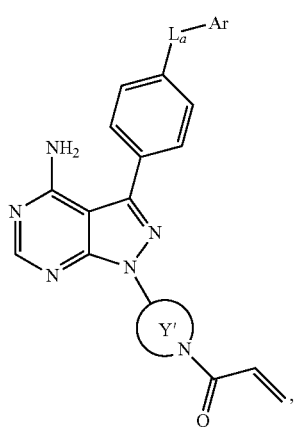

wherein $L_a$ is O; Ar is substituted or unsubstituted aryl; and Y' is a 5- or 6-membered heterocycloalkyl;
C is a fluorophore;
B is a linker moiety that links the irreversible Btk inhibitor moiety to the fluorophore;
X is a bond;
Y is selected from the group consisting of a bond, —O(C=O)—, —NR$^a$(C=O)—, —NR$^a$—, —O—, —S—, —S—S—, —O—NR$^a$—, —O(C=O)O—, —O(C=O)NR$^a$—, —NR$^a$(C=O)NR$^a$—, —N=CR$^a$—, —S(C=O)—, —S(O)—, and —S(O)$_2$; and
R$^a$ is H or alkyl.

2. The Btk activity probe of claim 1, wherein the linker moiety covalently links the irreversible Btk inhibitor moiety to the fluorophore.

3. The Btk activity probe of claim 1, wherein the cysteine residue is in the adenosine triphosphate (ATP) binding pocket of the Btk enzyme.

4. The Btk activity probe of claim 3, wherein the cysteine residue is Cys 481 of the Btk enzyme.

5. The Btk activity probe of claim 1, wherein the linker moiety is selected from a bond, an optionally substituted alkyl moiety, an optionally substituted heterocycle moiety, an optionally substituted amide moiety, a ketone moiety, an optionally substituted carbamate moiety, an ester moiety, or a combination thereof.

6. The Btk activity probe of claim 5, wherein the linker moiety comprises an optionally substituted heterocycle moiety.

7. The Btk activity probe of claim 6, wherein the optionally substituted heterocycle moiety comprises an optionally substituted piperazinyl moiety.

8. The Btk activity probe of claim 1, wherein the fluorophore is a 4,4-difluoro-1,3,5,7,8-pentamethyl-4-bora-3a,4a-diaza-s-indacene fluorophore.

9. The Btk activity probe of claim 1, wherein the fluorophore is a 4,4-difluoro-5,7-dimethyl-4-bora-3a,4a-diaza-s-indacene-3-propionic acid fluorophore.

10. The Btk activity probe of claim 1, wherein the irreversible Btk inhibitor moiety is:

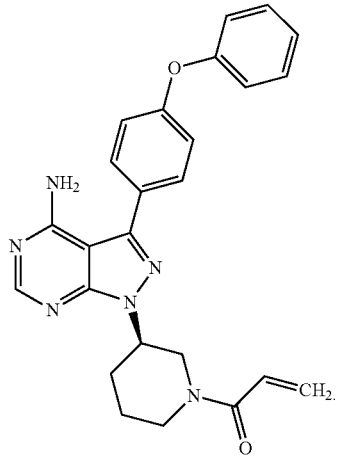 [SMILES: C=CC(=O)N1CCC[C@@H](n2nc(-c3ccc(Oc4ccccc4)cc3)c3c(N)ncnc32)C1]

11. The Btk activity probe of claim 1 having the structure:

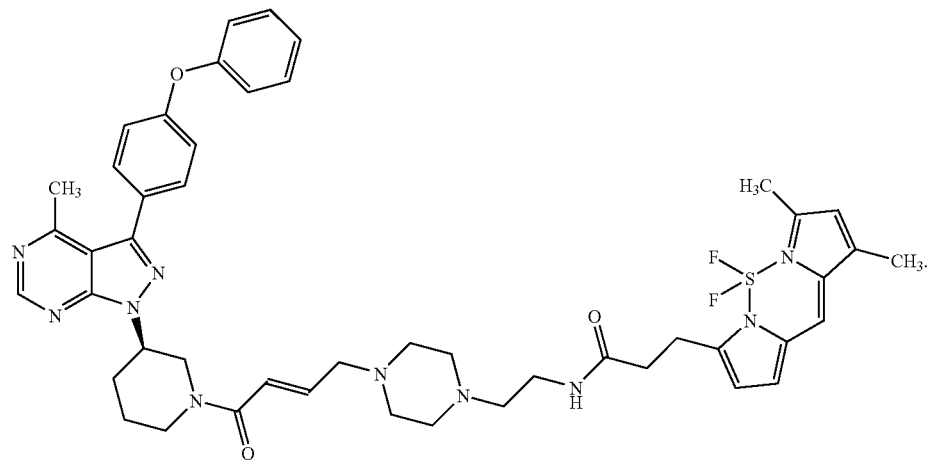

12. The Btk activity probe of claim 1, wherein the probe selectively labels a phosphorylated conformation of Btk.

13. The Btk activity probe of claim 12, wherein the phosphorylated conformation of Btk is an active form of Btk.

14. The Btk activity probe of claim 1, wherein the probe is cell permeable.

15. The Btk activity probe of claim 1, wherein the irreversible Btk inhibitor moiety is:

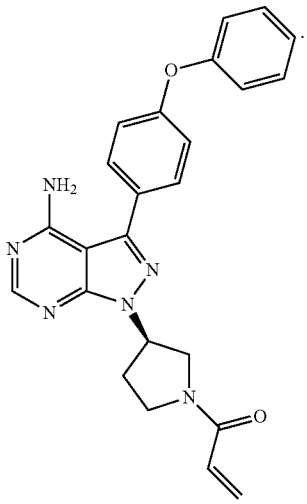 [SMILES: C=CC(=O)N1CC[C@@H](n2nc(-c3ccc(Oc4ccccc4)cc3)c3c(N)ncnc32)C1]

16. The Btk activity probe of claim 1 having the structure:

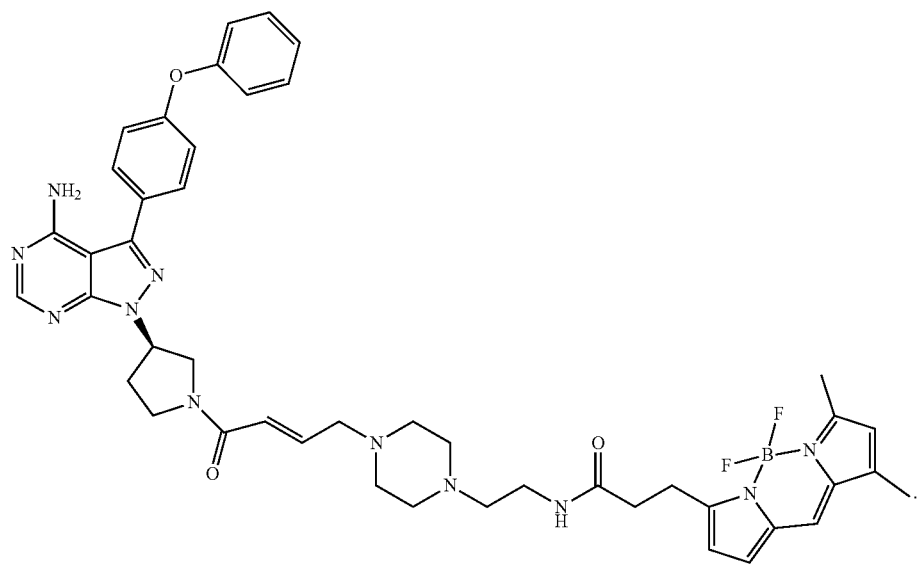

* * * * *

SEQUENCE LISTING

```
<160> NUMBER OF SEQ ID NOS: 12

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: biotin-Ala
<220> FEATURE:
<223> OTHER INFORMATION: c-term amidation

<400> SEQUENCE: 1

Ala Val Leu Glu Ser Glu Glu Glu Leu Tyr Ser Ser Ala Arg Gln
1               5                   10                  15

<210> SEQ ID NO 2
<211> LENGTH: 6
<212> TYPE: PRT
<213> ORGANISM: Artificial Sequence
<220> FEATURE:
```

<223> OTHER INFORMATION: Description of Artificial Sequence: Synthetic
      6x His tag

<400> SEQUENCE: 2

His His His His His His
  1               5

<210> SEQ ID NO 3
<211> LENGTH: 25
<212> TYPE: PRT
<213> ORGANISM: Homo sapiens

<400> SEQUENCE: 3

Arg Pro Ile Phe Ile Ile Thr Glu Tyr Met Ala Asn Gly Cys Leu Leu
  1               5                  10                  15

Asn Tyr Leu Arg Glu Met Arg His Arg
             20                  25

<210> SEQ ID NO 4
<211> LENGTH: 25
<212> TYPE: PRT
<213> ORGANISM: Homo sapiens

<400> SEQUENCE: 4

Tyr Pro Leu Tyr Leu Val Thr Glu Tyr Leu Ser Asn Gly Cys Leu Leu
  1               5                  10                  15

Asn Tyr Ile Arg Ser His Gly Lys Gly
             20                  25

<210> SEQ ID NO 5
<211> LENGTH: 25
<212> TYPE: PRT
<213> ORGANISM: Homo sapiens

<400> SEQUENCE: 5

Lys Pro Ile Tyr Ile Val Thr Glu Phe Met Glu Arg Gly Cys Leu Leu
  1               5                  10                  15

Asn Phe Leu Arg Gln Arg Gln Gly His
             20                  25

<210> SEQ ID NO 6
<211> LENGTH: 25
<212> TYPE: PRT
<213> ORGANISM: Homo sapiens

<400> SEQUENCE: 6

Lys Pro Leu Tyr Ile Val Thr Glu Phe Met Glu Asn Gly Cys Leu Leu
  1               5                  10                  15

Asn Tyr Leu Arg Glu Asn Lys Gly Lys
             20                  25

<210> SEQ ID NO 7
<211> LENGTH: 25
<212> TYPE: PRT
<213> ORGANISM: Homo sapiens

<400> SEQUENCE: 7

Ala Pro Ile Cys Leu Val Phe Glu Phe Met Glu His Gly Cys Leu Ser
  1               5                  10                  15

Asp Tyr Leu Arg Thr Gly Arg Gly Leu
             20                  25

```
<210> SEQ ID NO 8
<211> LENGTH: 25
<212> TYPE: PRT
<213> ORGANISM: Homo sapiens

<400> SEQUENCE: 8

Ser Thr Val Gln Leu Ile Thr Gln Leu Met Pro Phe Gly Cys Leu Leu
  1               5                  10                  15

Asp Tyr Val Arg Glu His Lys Asp Asn
            20                  25

<210> SEQ ID NO 9
<211> LENGTH: 25
<212> TYPE: PRT
<213> ORGANISM: Homo sapiens

<400> SEQUENCE: 9

Ser Thr Val Gln Leu Val Thr Gln Leu Met Pro Tyr Gly Cys Leu Leu
  1               5                  10                  15

Asp His Val Arg Glu Asn Arg Gly Arg
            20                  25

<210> SEQ ID NO 10
<211> LENGTH: 25
<212> TYPE: PRT
<213> ORGANISM: Homo sapiens

<400> SEQUENCE: 10

Pro Thr Ile Gln Leu Val Thr Gln Leu Met Pro His Gly Cys Leu Leu
  1               5                  10                  15

Glu Tyr Val His Glu His Lys Asp Asn
            20                  25

<210> SEQ ID NO 11
<211> LENGTH: 25
<212> TYPE: PRT
<213> ORGANISM: Homo sapiens

<400> SEQUENCE: 11

Pro Glu Leu Arg Leu Val Met Glu Tyr Leu Pro Ser Gly Cys Leu Arg
  1               5                  10                  15

Asp Phe Leu Gln Arg His Arg Ala Arg
            20                  25

<210> SEQ ID NO 12
<211> LENGTH: 25
<212> TYPE: PRT
<213> ORGANISM: Homo sapiens

<400> SEQUENCE: 12

Glu Pro Ile Tyr Ile Val Thr Glu Tyr Met Ala Arg Gly Cys Leu Leu
  1               5                  10                  15

Asp Phe Leu Lys Thr Asp Glu Gly Ser
            20                  25
```